(12) United States Patent
Nishino et al.

(10) Patent No.: US 8,265,225 B2
(45) Date of Patent: Sep. 11, 2012

(54) RADIATION IMAGING SYSTEM, POWER SUPPLYING APPARATUS, CHARGING APPARATUS, AND RADIATION IMAGING METHOD

(75) Inventors: Naoyuki Nishino, Kanagawa (JP); Keizo Katayama, Kanagawa (JP); Atsushi Yamazaki, Kanagawa (JP); Yasunori Ohta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 431 days.

(21) Appl. No.: 12/699,893

(22) Filed: Feb. 4, 2010

(65) Prior Publication Data
US 2010/0202586 A1 Aug. 12, 2010

(30) Foreign Application Priority Data

Feb. 12, 2009 (JP) ................................. 2009-029802

(51) Int. Cl.
*H05G 1/64* (2006.01)
*H05G 1/10* (2006.01)
(52) U.S. Cl. ....... 378/98.5; 378/98.8; 378/102; 378/165
(58) Field of Classification Search ..................... 378/91, 378/98, 98.5, 98.8, 102, 103, 165
See application file for complete search history.

(56) References Cited

U.S. PATENT DOCUMENTS

| 7,092,491 | B2 * | 8/2006 | Okoda | 378/162 |
|---|---|---|---|---|
| 7,419,467 | B2 * | 9/2008 | Tsai | 600/109 |
| 7,427,769 | B2 * | 9/2008 | Haug et al. | 250/581 |
| 7,783,008 | B2 * | 8/2010 | Jabri | 378/98.5 |
| 2006/0261296 | A1 * | 11/2006 | Heath et al. | 250/580 |
| 2008/0130837 | A1 * | 6/2008 | Heath et al. | 378/205 |
| 2008/0240358 | A1 * | 10/2008 | Utschig et al. | 378/107 |
| 2009/0039276 | A1 * | 2/2009 | Ohta et al. | 250/370.08 |
| 2009/0060136 | A1 * | 3/2009 | Tamakoshi | 378/91 |
| 2010/0104066 | A1 * | 4/2010 | Foos et al. | 378/62 |
| 2010/0202586 | A1 * | 8/2010 | Nishino et al. | 378/62 |
| 2011/0110496 | A1 * | 5/2011 | Foos et al. | 378/98.5 |

FOREIGN PATENT DOCUMENTS

| JP | 2001-224579 A | 8/2001 |
|---|---|---|
| JP | 2003-030324 A | 1/2003 |

* cited by examiner

*Primary Examiner* — Thomas R Artman
(74) *Attorney, Agent, or Firm* — SOLARIS Intellectual Property Group, PLLC

(57) ABSTRACT

The present invention provides a radiation imaging system, a power supplying apparatus, a charging apparatus, and a radiation imaging method that can prevent misidentification of an imaging subject to be imaged without requiring a large-scale configuration. Namely, a power supplying apparatus which is detachably mounted to an electronic cassette is provided with a display section that displays imaging subject information associated with an imaging subject.

15 Claims, 12 Drawing Sheets

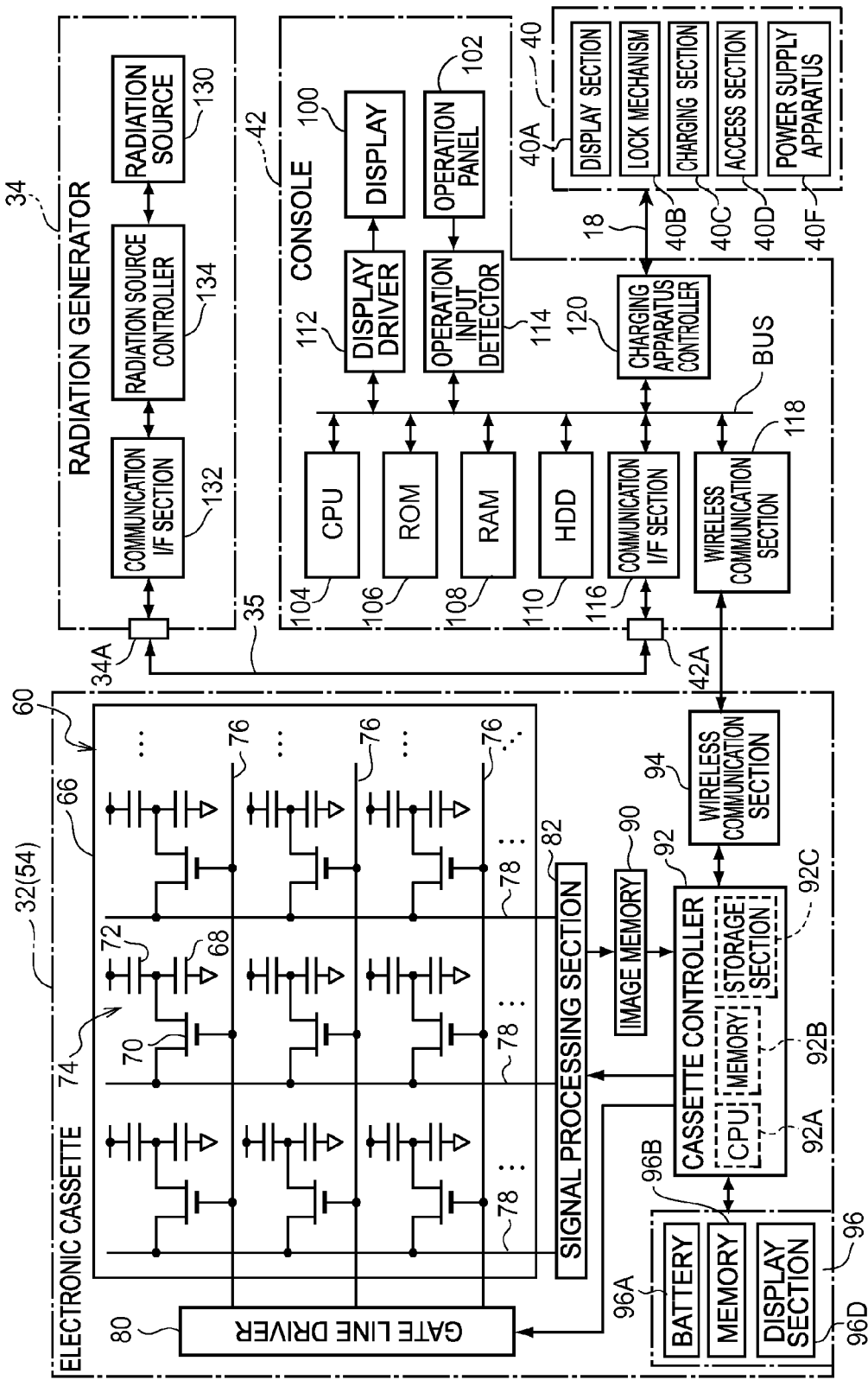

MR TARO YAMADA (01-001, MALE)

· IMAGING PORTION: ARM PORTION   · CASSETTE TO BE USED: SMALL
· THE NUMBER OF IMAGES: FOUR      · POSTURE: STANDING  · · ·

RADIATION IMAGING SYSTEM, POWER SUPPLYING APPARATUS, CHARGING APPARATUS, AND RADIATION IMAGING METHOD

CROSS-REFERENCE TO RELATED APPLICATION

This application claims priority under 35 USC 119 from Japanese Patent Application No. 2009-029802, filed on Feb. 12, 2009, the disclosure of which is incorporated by reference herein.

BACKGROUND OF THE INVENTION

1. Field of the Invention

The present invention relates to a radiation imaging system, a power supplying apparatus, a charging apparatus, and a radiation imaging method. More particularly, the present invention relates to a radiation imaging system for imaging a radiation image represented by radiation passing through an imaging subject, a power supplying apparatus and a charging apparatus used in the radiation imaging system, and a radiation imaging method used by the radiation imaging system.

2. Description of the Related Art

Recently, radiation detectors such as FPD (Flat Panel Detector), which have a radiation sensitive layer disposed on a TFT (Thin Film Transistor) active matrix substrate which can directly convert radiation to digital data, have come into practical use. Further, a portable radiation imaging device (hereinafter, also called an "electronic cassette") for imaging a radiation image represented by irradiated radiation using the radiation detector has come into practical use. The electronic cassette employs, as a system for converting radiation, for example, either an indirect-conversion-type radiation detector that converts radiation to light by a scintillator and thereafter converts radiation to charges by a semiconductor layer of a photodiode, or a direct-conversion-type radiation detector that directly converts radiation to charges by a semiconductor layer of amorphous silicon. Note that, various materials may be used for the semiconductor layer in the above respective types.

In the conventional radiation imaging apparatuses, cables for supplying operation power and cables for transferring image information, obtained by imaging, to higher-level devices were provided. Therefore, in the conventional art, a portable apparatus could not effectively make use of its merit.

Japanese Patent Application Laid-Open (JP-A) No. 2001-224579 discloses an X-ray imaging apparatus. The X-ray imaging apparatus includes a wireless signal transmission device, an X-ray detector, a battery, and an image processing device. The wireless signal transmission device transmits wireless signals to an X-ray tube for irradiating X-rays to an examinee. The X-ray detector includes a signal collection section for collecting detected data outputted from an X-ray detection element when X-rays are irradiated. The battery is accommodated in the X-ray detector, and supplies power to the X-ray detector. The image processing device includes a wireless receiver for receiving a wireless signal. The battery mounted detachably to the X-ray detector. Further, the X-ray detector includes a spare battery.

According to the above X-ray imaging apparatus, the power supply battery is configured to be mounted detachably to the X-ray detector. Accordingly, since the power supply cable need not be provided in the X-ray imaging apparatus disclosed in JP-A No. 2001-224579, portability of the X-ray imaging apparatus is improved.

Incidentally, in a department of radiology of a hospital, a reception table for accepting radiation imaging is located separately from an imaging room in which the radiation imaging is actually performed to efficiently perform the radiation imaging to plural patients. In this case, a case where an examinee (subject) is misidentified with other examinee in the imaging room may occur.

To prevent such case, JP-A No. 2003-30324 discloses a patient identifying method. This patient identifying method includes an initial registering step that obtains a personal recognition data and patient information, and that registers the obtained data and information into a database, while associating the personal recognition data and the patient information with each other. Further, the patient identifying method includes a collating step that obtains the personal recognition data from the patient when confirming the patient, and that collates the personal recognition data with the personal recognition data registered in the database. Furthermore, the patient identifying method includes, a step that output a collation result of the collating step, wherein when the personal recognition data registered in the database matches with the personal recognition data obtained when confirming the patient, output the registered patient information associated with the matched personal recognition data. Note that, the personal recognition data indicates biological individual difference, such as face of the patient, finger prints, iris, or voice print. Further, the patient data indicates the name of the patient, the patient ID, date of birth, and the like.

However, the patient identifying method disclosed in JP-A No. 2003-30324 uses a personal recognition data that indicates biological individual difference. Therefore, in the above technique, the system configuration may become large.

SUMMARY OF THE INVENTION

The present invention provides a radiation imaging system, a power supplying apparatus, a charging apparatus, and a radiation imaging method that prevents misidentified of the imaging subject without requiring a large configuration.

A first aspect of the invention is a radiation imaging system including: a radiation imaging apparatus that images a radiation image represented by radiation that passes through an imaging subject; and a power supplying apparatus, mounted detachably to the radiation imaging apparatus, and including a chargeable power supply section that supplies drive power to the radiation imaging apparatus, and a display section that displays an imaging subject information associated with the imaging subject.

According to a radiation imaging system of a first aspect of the present invention, a radiation image shown by radiation that pass through an imaging subject, is imaged by the radiation imaging apparatus.

Further, in the first aspect of the present invention, driving power is supplied to the radiation imaging apparatus form a power supply section which can be charged (stored with power) by the power supplying apparatus which is detachably mounted to the radiation imaging apparatus.

The power supplying apparatus according to the invention is provided with a display section that displays the imaging subject information associated with the imaging subject.

Therefore, in the first aspect of the invention, when the power supplying apparatus is mounted on the radiation imaging apparatus, the imaging subject information is displayed on the display section of the power supplying apparatus. Accordingly, the first aspect of the present invention can confirm whether the imaging subject to be imaged by the radiation imaging apparatus matches with the subject shown in the imaging subject information by referring to the imaging subject information. With this configuration, the radiation imaging system of the first aspect of the present invention can prevent the misidentification of the imaging subject.

Further, the present invention, unlike the case of using the personal recognition data that indicates biological individual differences, does not need a large configuration.

Accordingly, in the radiation imaging system of the first aspect of the invention, a power supplying apparatus, detachable from the radiation imaging apparatus, is provided with the display section that displays the imaging subject information associated with subject. Therefore, the first aspect of the invention can prevent the misidentification of the imaging subject without requiring a large configuration.

Note that, the display by the display section includes visible display by a display such as a liquid crystal display or an organic EL display, but also includes audible indication by a sound playback apparatus or the like.

In a second aspect of the invention, in the first aspect, the power supplying apparatus may further include a storing section that stores the imaging subject information, and the display section may display the stored imaging subject information. With this configuration, in the second aspect of the invention, the power supplying apparatus holds the imaging subject information. Accordingly, the second aspect of the invention can improve the convenience of the user.

Note that, the storage section includes a semiconductor storage device such as a RAM (Random Access Memory), an EEPROM (Electrically Erasable and Programmable Read Only Memory), and a flash EEPROM (Flash EEPROM), a portable recording medium such as an XD Picture Card® and an SD Memory®, or a fixed recording medium such as a hard disk.

In a third aspect of the invention, in the second aspect, may further include a charging apparatus including, a charging section that charges the power supplying apparatus when the power supplying apparatus is mounted to the charging apparatus, and a writing section that writes the imaging subject information into the storing section when the power supplying apparatus is mounted to the charging apparatus, before the power supplying apparatus is mounted to the radiation imaging apparatus. With this configuration, the third aspect of the present invention can simplify the writing of the imaging subject information in the storage section of the power supplying apparatus. Accordingly, the radiation imaging system of the second aspect of the present invention can prevent the misidentification of the imaging subject.

In a fourth aspect of the invention, in the third aspect, wherein the storing section may further store image information obtained by imaging performed by the radiation imaging apparatus, and the charging apparatus may further include a reading section that reads the stored image information when the power supplying apparatus is mounted. With this configuration, in the fourth aspect of the present invention, the image information obtained by imaging is transferred to higher-level devices through the charging apparatus. Therefore, the third aspect of the present invention can reliably perform the transfer of the imaged data when compared to a case where the transfer is performed by wireless.

In a fifth aspect of the invention, in the third aspect, the radiation imaging apparatus may further include a transmitting section that, before the imaging subject is imaged, transmits the stored imaging subject information when the power supplying apparatus is mounted to the radiation imaging apparatus; a receiving section that receives the transmitted imaging subject information; a determining section that determines whether the received imaging subject information is information that corresponds to the imaging subject; and a process executing section that executes a predetermined process based on the result of the determination. With the configuration, in the fifth aspect of the invention, a process is performed according to a result of confirmation of whether the imaging subject is a person whose imaging is planed. Accordingly, the fourth aspect of the present invention can prevent the misidentification of the imaging subject more reliably.

In a sixth aspect of the invention, in the fifth aspect, when it is determined that the imaging subject information is not the information that corresponds to the imaging subject, the process execution section may execute at least one of an imaging inhibition process or an occurrence of failure notification process as the predetermined process. With this configuration, the sixth aspect of the present invention can prevent the misidentification of the imaging subject more reliably.

In a seventh aspect of the invention, in the fifth aspect, the determination section may determine whether the received imaging subject information is the information that corresponds to the imaging subject by determining whether the imaging subject information matches with the imaging subject information written in the storing section. With this configuration, the seventh aspect of the present invention can prevent the misidentification of the imaging subject more reliably.

In an eighth aspect of the invention, in the third aspect, the imaging subject information may include specific information for specifying the imaging subject. With this configuration, the eighth aspect of the present invention can confirm the imaging subject more simply. As a result, the seventh aspect of the present invention can prevent the misidentification of subject more simply. Note that, the specific information includes a name of the imaging subject and ID (Identification) information previously given to the imaging subject.

In a ninth aspect of the invention, in the eighth aspect, the imaging subject information may further include information showing an imaging condition of the imaging subject. With this configuration, the ninth aspect of the present invention can improve the convenience of the user.

In a tenth aspect of the invention, in the third aspect, the charging apparatus may further include a detachment inhibiting section that inhibits detachment of the power supplying apparatus when charging of the power supply section has not been completed when the power supplying apparatus is mounted to the charging apparatus. With this configuration, the tenth aspect of the present invention can prevent the use of the power supplying apparatus which has not yet been charged. As a result, the tenth aspect of the present invention can improve the convenience of the user.

In an eleventh aspect of the invention, in the third aspect, the charging apparatus may further include a communication section that performs communication through a power line of a commercial power source. With this configuration, in the eleventh aspect of the present invention, the charging apparatus can be installed to any location that has a supply section (outlet) of commercial power. As a result, the eleventh aspect of the present invention can prevent the misidentification of subject more securely.

In a twelfth aspect of the invention, in the first aspect, the radiation imaging apparatus may be an electronic cassette. With this configuration, the twelfth aspect of the invention can prevent the misidentification of the imaging subject without requiring a large configuration.

In a thirteenth aspect of the invention is a power supplying apparatus including: a chargeable power supply section that supplies drive power to a radiation imaging apparatus that images a radiation image represented by radiation that passes through an imaging subject; and a display section that displays imaging subject information associated with the imaging subject, wherein the power supplying apparatus is mounted detachably to the radiation imaging apparatus.

According to the thirteenth aspect of the present invention, the power supplying apparatus operates likewise to the power supplying apparatus in the radiation imaging system according to the first aspect of the present invention. Therefore, when the power supplying apparatus according to the thirteenth aspect of the present invention is used together with the radiation imaging apparatus, the power supplying apparatus can prevent the misidentification of subject without requiring a large configuration, likewise to the radiation imaging system.

A fourteenth aspect of the invention is a charging apparatus including: a charging section that charges a chargeable power supply section of a power supplying apparatus when the power supplying apparatus is mounted to the charging apparatus, the power supplying apparatus including, the power supply section that supplies drive power to the radiation imaging apparatus that images a radiation image represented by radiation that passes through an imaging subject, a display section that displays imaging subject information associated with the imaging subject, a storing section that stores the imaging subject information; and a writing section that writes the imaging subject information into the storing section when the power supplying apparatus is mounted to the charging apparatus, before the power supplying apparatus is mounted to the radiation imaging apparatus.

According to the fourteenth aspect of the present invention, the charging apparatus operates likewise to the charging apparatus in the radiation imaging system according to the third aspect of the present invention. Therefore, when the charging apparatus according to the fourteenth aspect of the present invention is used together with the radiation imaging apparatus and the power supplying apparatus, the charging apparatus can prevent the misidentification of subject without requiring a large configuration, likewise to the radiation imaging system.

A fifteenth aspect of the invention is a method for radiation imaging in a radiation imaging system including a radiation imaging apparatus that images a radiation image represented by radiation that passes through an imaging subject, a power supplying apparatus, mounted detachably to the radiation imaging apparatus, and including a chargeable power supply section that supplies drive power to the radiation imaging apparatus, a display section that displays imaging subject information associated with the imaging subject, and a storing section that stores the imaging subject information, a charging apparatus including a charging section that charges the power supplying section when the power supplying apparatus is mounted to the charging apparatus, the method including: writing the imaging subject information in the storing section by the charging apparatus when the power supplying apparatus is mounted to the charging apparatus, before the power supplying apparatus is mounted to the radiation imaging apparatus; transmitting the imaging subject information to the radiation imaging apparatus when the power supplying apparatus is mounted to the radiation imaging apparatus, before an imaging subject is imaged; receiving the transmitted the imaging subject information; determining whether the received imaging subject information corresponds to the imaging subject; and executing a predetermined process based on a result of the determination.

According to the fifteenth aspect of the present invention, the radiation imaging method operates likewise to the radiation imaging system according to the fifth aspect of the present invention. Therefore, the radiation imaging method according to the fifteenth aspect of the present invention can prevent the misidentification of the imaging subject without requiring a large configuration, likewise the radiation imaging system.

According to the present invention, the misidentification of the imaging subject can be prevented without requiring a large configuration.

BRIEF DESCRIPTION OF THE DRAWINGS

Exemplary embodiments of the present invention will be described in detail based on the following figures, wherein:

FIG. 6 is a block diagram showing a configuration of a main portion of an electric system of the radiation imaging system according to the exemplary embodiment of the present invention;

FIG. 9 is a schematic diagram showing an example of an information displayed on the power supplying apparatus when the examinee information writing process program according to the exemplary embodiment is executed;

DETAILED DESCRIPTION OF THE INVENTION

An exemplary embodiment of the present invention will be explained below in detail with reference to the drawings. Note that, hereafter an example will be explained when the present invention is applied to a radiation information system that integrally manages the information treated in a department of radiology in a hospital.

Figure 1:
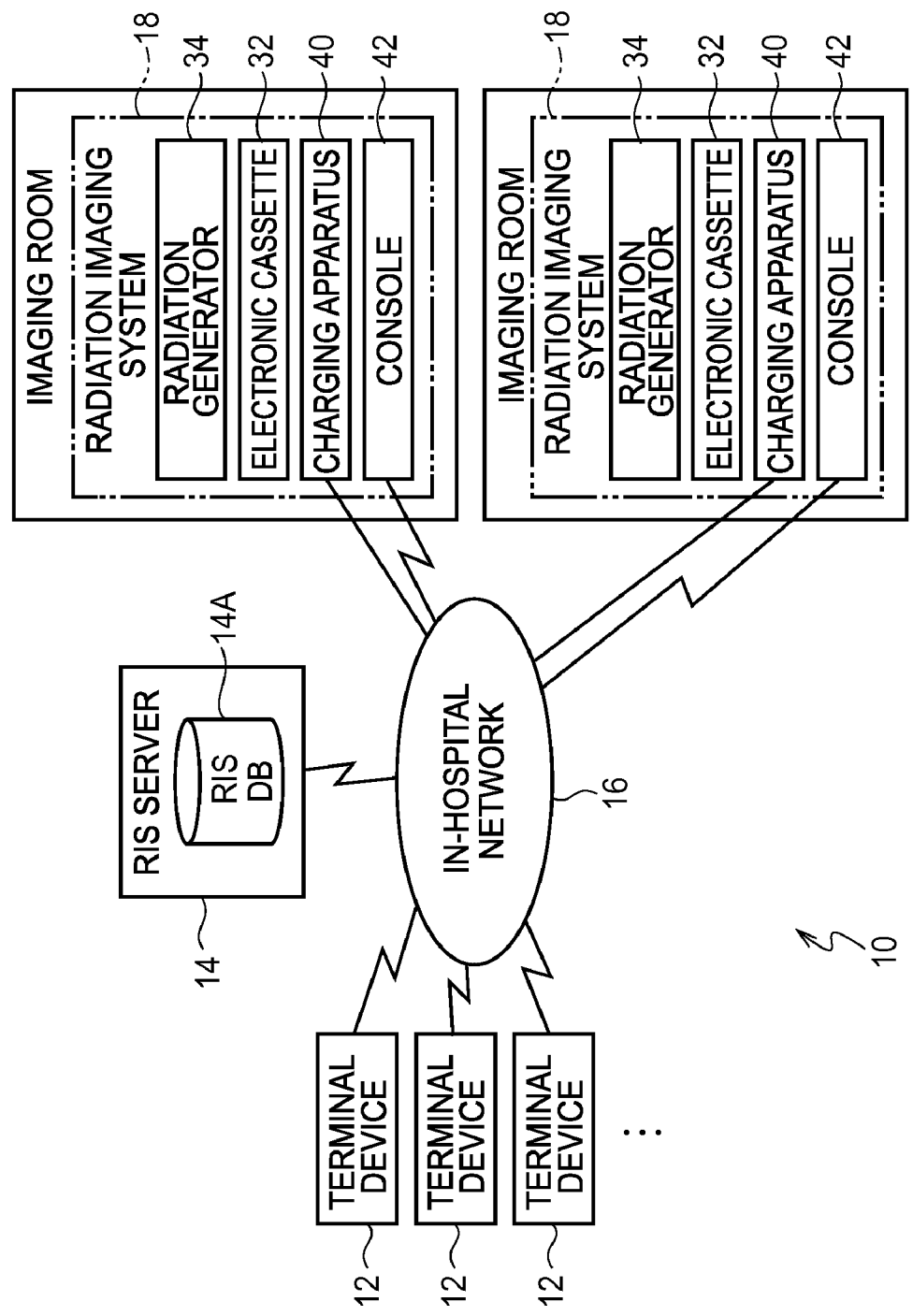
FIG. 1 is a block diagram showing a configuration of a radiation information system according to an exemplary embodiment of the present invention.

Firstly, a configuration of the radiation information system (hereinafter, called "a RIS (Radiology Information System)") 10 according to the exemplary embodiment will be explained with reference to FIG. 1.

The RIS 10 is a system for performing an information management such as a reservation of medical examination, a diagnosis record, and the like, in the department of radiology. The RIS 10 configures a part of a hospital information system (hereinafter, called "HIS" (Hospital Information System)).

The RIS 10 includes plural imaging request terminal devices (hereinafter, called "terminal devices") 12, a RIS server 14, and a radiation imaging system (hereinafter, called "imaging system") 18. The RIS 10 is configured by being connected to an in-hospital network 16 including a wired or a wireless LAN (Local Area Network) or the like. The radiation imaging system is installed in each of the radiation imaging room (or operating room) in the hospital. Note that, the RIS 10 configures a part of HIS installed in the same hospital. Further, a HIS server (not shown) that entirely manages the HIS is connected to the in-hospital network 16.

The terminal devices 12 are used by a doctor or a radiological technologist to input and browse diagnosis information, a reservation of the facilities, or the like. An imaging request and an imaging reservation of a radiation image are performed through the terminal devices 12. The respective terminal devices 12 include personal computers having display sections. The respective terminal devices 12 may mutually communicate with each other through the RIS server 14 and the in-hospital network 16.

On the other hand, the RIS server 14 accepts imaging requests from the respective terminal devices 12 and manages an imaging schedule of radiation images of the imaging system 18. Further, the RIS server 14 includes a database 14A.

The database 14A includes information associated with patients (hereinafter, called "patient information"), information associated with an electronic cassette 32 (hereinafter, called "electronic cassette information"), and an environment information. The patient information includes, attribute information of the patient (name, ID, gender, birth day, age, blood type, body weight, and the like), medical history, consultation history, and radiation images imaged in the past. The electronic cassette information relates to the electronic cassette 32 used for the imaging system 18 and includes identification number, type, size, sensitivity, usable imaging portions (contents of imaging request that may be coped with), usable power supplying apparatus, start date of use, and number of times used. The environment information shows an environment which the radiation image is imaged by using the electronic cassette 32, i.e., an environment in which the electronic cassette 32 is used (as an example, a radiation imaging room, an operating room, and the like).

The database 14A includes an imaging menu which is an information showing a portion of a body of a patient to be imaged (hereinafter, called "imaging portion"), a type of the electronic cassette to be used (hereinafter, called a "cassette in use"), the number of images, a posture of a patient when imaging (in the exemplary embodiment, a lying position or a standing position), and a condition when radiation imaging is performed such as an irradiation direction in which radiation are irradiated to a patient.

The imaging system 18 performs radiation imaging in response to an operation by the doctor or the radiological technologist based on instructions from the RIS server 14. The imaging system 18 includes a radiation generator 34, the electronic cassette 32, a charging apparatus 40, and a console 42. The radiation generator 34 irradiates radiation X including a radiation dose set according to an exposure condition (refer also to FIG. 3) from a radiation source 130 (also refer to FIG. 2), to a patient. The electronic cassette 32 contains a radiation detector 60 (also refer to FIG. 3) that generates charges by absorbing the radiation X that passed through an imaging portion of a patient, and that creates image information showing a radiation image based on the amount of the generated charges. The charging apparatus 40 charges the power supplying apparatus 96 (also refer to FIG. 3) mounted detachably to the electronic cassette 32. The console 42 controls the electronic cassette 32, the radiation generator 34, and the charging apparatus 40.

The console 42 obtains various information included in the database 14A from the RIS server 14, and stores the obtained information to a HDD (hard disk drive) 110 (also refer to FIG. 6). Further, the console 42 controls the electronic cassette 32, the radiation generator 34, and the charging apparatus 40 based on the obtained information.

Figure 2:
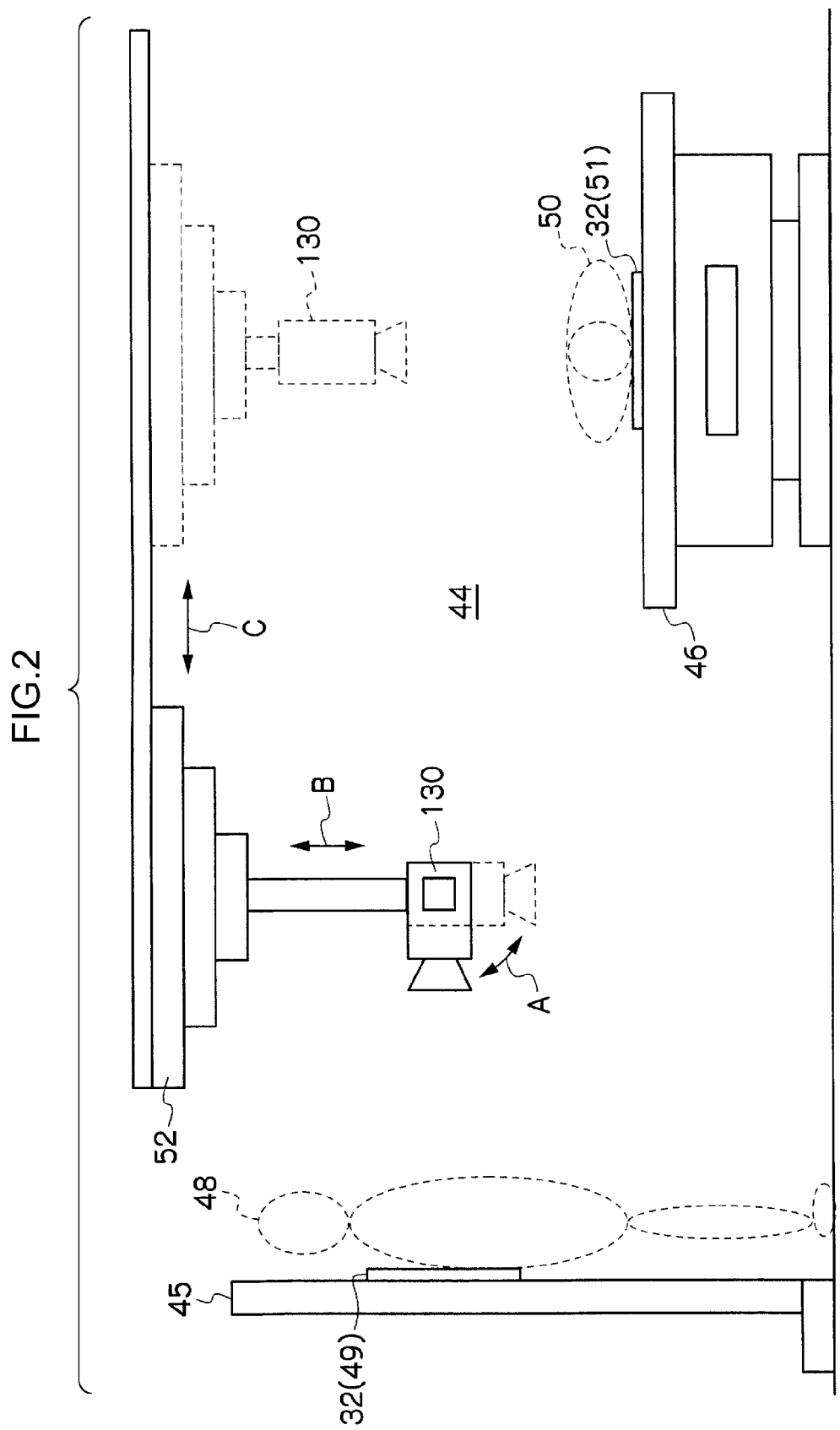
FIG. 2 is a side view showing an example layout of a radiation imaging system according to the exemplary embodiment of the present invention in a radiation imaging room.

FIG. 2 shows an example of a layout of the imaging system 18 according to the exemplary embodiment in a radiation imaging room 44.

As shown in FIG. 2, a rack 45 and a bed 46 are installed in the radiation imaging room 44. The rack 45 holds the electronic cassette 32 when radiation imaging is performed at a standing position. A patient lies on the bed 46 when the radiation imaging is performed at a lying position. A front space of the rack 45 is used as an imaging position 48 of the patient when the radiation imaging is performed at the standing position. An upper space of the bed 46 is used as an imaging position 50 of the patient when the radiation imaging is performed at the lying position.

Further, to permit the radiation from a single radiation source 130 to perform the radiation imaging at the standing position and at the lying position, a supporting/moving mechanism 52 for supporting the radiation source 130 is installed in the radiation imaging room 44. The supporting/moving mechanism 52 supports the radiation source 130 so that it can rotate about a horizontal axis (arrow A direction of FIG. 2), move in a vertical direction (arrow B direction of FIG. 2), and further move in a horizontal direction (arrow C direction of FIG. 2). The supporting/moving mechanism 52 includes a drive source (not shown) for rotating the radiation source 130 about the horizontal axis, a drive source (not shown) for moving the radiation source 130 in the vertical direction, and a drive source (not shown) for moving the radiation source 130 in the horizontal direction, respectively.

When an imaging posture is the standing position, the electronic cassette 32 is positioned at a predetermined position 49 held by the rack 45, and when the imaging posture is the lying position, the electronic cassette 32 is positioned at a predetermined position 51 located below an imaging portion of the bed 46.

The radiation imaging room 44 according to the exemplary embodiment is provided with a reception table and an imaging management room (not shown) separately from a region in which the radiation imaging is actually performed (hereinafter, called an "imaging region"). The rack 45, the bed 46, the supporting/moving mechanism 52, the radiation source 130, and the like are installed in the imaging region. The reception table is disposed at the position facing an outside of the radiation imaging rooms 44 (on a path side in a building). The imaging management room is provided with a partition wall that separates the imaging region from the imaging management room and that can suppress the enter of the radiation X, and is provided with a window disposed at a position in which the imaging region can be viewed and that can reduce the passing amount of the radiation X there through.

In the imaging system 18 according to the exemplary embodiment, the charging apparatus 40 and the console 42 are disposed in the imaging management room. A patient to whom the radiation imaging is performed in the radiation imaging room 44 is registered in the imaging management room.

In the imaging system 18 according to the exemplary embodiment, various information are transmitted and received by a wired communication through a cable connecting the radiation generator 34 and the console 42. However, the cable is not shown in FIG. 2. Further, in the imaging system 18 according to the exemplary embodiment, various information are transmitted and received between the electronic cassette 32 and the console 42 by a wireless communication.

Note that, the electronic cassette 32 is not to be used only in the radiation imaging room and the operating room. The electronic cassette 32 may be also used in, for example, a health check, doctor's rounds in the hospital, and the like, due to its portability.

Figure 3:
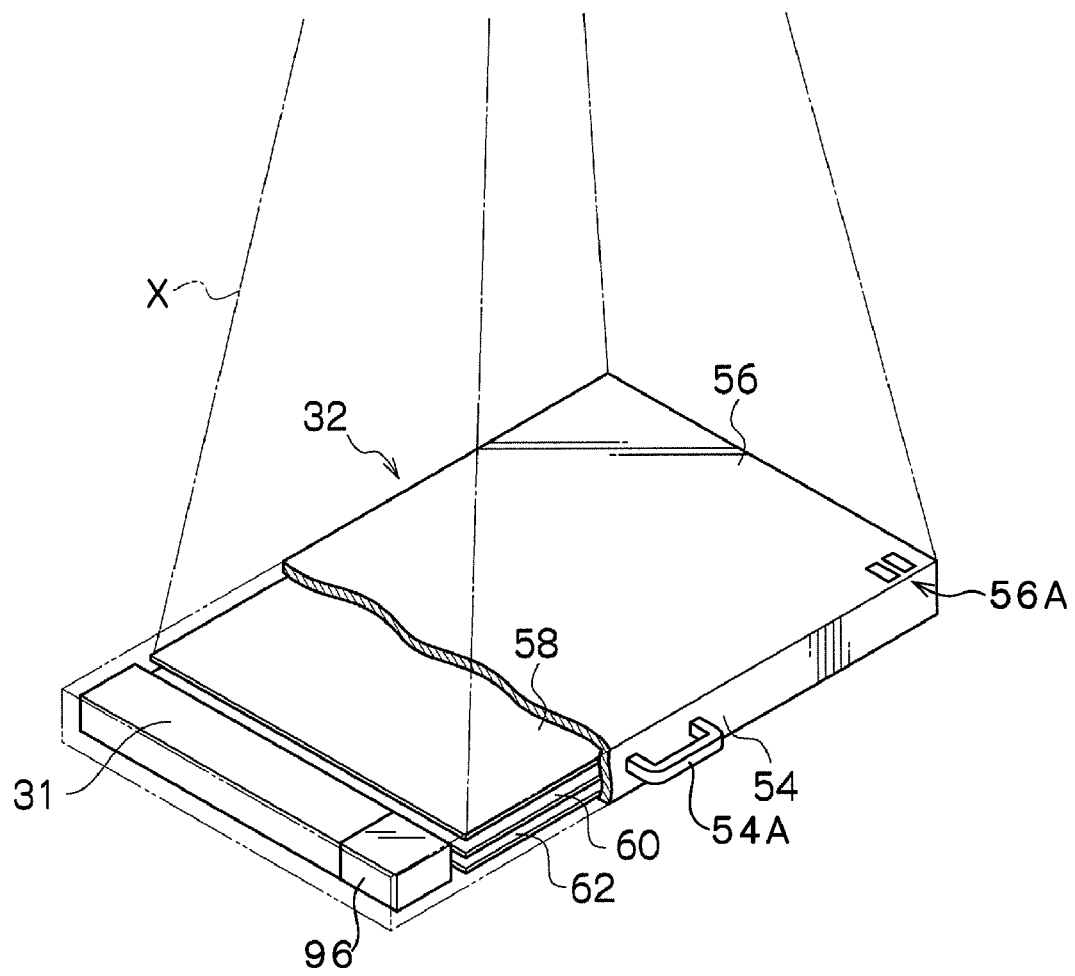
FIG. 3 is a transparent perspective view showing a configuration of an electronic cassette according to the exemplary embodiment of the present invention.

FIG. 3 shows internal configuration of the electronic cassette 32 according to the exemplary embodiment.

As shown in FIG. 3, the electronic cassette 32 includes a chassis 54 formed of a material that causes the radiation X to pass there through and is structured to have waterproof property and sealing property. When the electronic cassette 32 is used in the operating room and the like, there is a possibility for blood or other bacteria to adhere thereto. Therefore, in the exemplary embodiment, the electronic cassette 32 is configured to have waterproof property and sealing property. With this configuration, in the exemplary embodiment, a single electronic cassette 32 may be repeatedly used by being pasteurized and rinsed.

A grid 58, the radiation detector 60, and a lead sheet 62 are sequentially disposed in the chassis 54 from a radiation surface 56 side of the chassis 54 to which the radiation X are irradiated. The grid 58 removes scattered radiation of the radiation X scattered by the patient. The radiation detector 60 detects the radiation X passing through the patient. The lead sheet 62 absorbs the back scattered rays of the radiation X. In a different exemplary embodiment, the radiation surface 56 of the chassis 54 may be arranged as the grid 58.

Further, an electronic circuit and a case 31 are provided at one end side of the chassis 54. The electronic circuit includes a microcomputer. The case 31 accommodates the power supplying apparatus 96 which can be charged and mounted detachably. The radiation detector 60 and the electronic circuit are operated by the power supplied from the power supplying apparatus 96 disposed in the case 31. To avoid the various circuits accommodated in the case 31 from being damaged by the irradiation of the radiation X, a lead sheet and the like are preferably disposed on the radiation surface 56 side of the case 31. Note that, the electronic cassette 32 according to the exemplary embodiment is formed in a rectangular form whose radiation surface 56 is rectangle, and the case 31 is disposed to one end in a longer direction of the rectangle.

A display section 56A (not shown) is disposed at a predetermined position of an external wall of the chassis 54. The display section 56A displays, operating states of the electronic cassette 32 such as on/off state (turned on/off state) of a power supply switch, operation modes such as "ready state", "data transmitted", and remaining capacity of the power supplying apparatus 96. Note that, in the electronic cassette 32 according to the exemplary embodiment, a light emission diode is applied as the display section 56A. However, in the present invention, the display section 56A is not limited to the light emission diode. A light emission device other than the light emission diode, a liquid crystal display, an organic EL display and the like, may be applied as the display section 56A.

Further, a grip 54A is disposed at a predetermined position of the external wall of the chassis 54 so that it can be gripped when the electronic cassette 32 is moved. Note that, in the electronic cassette 32 according to the exemplary embodiment, the grip 54A is disposed at a central portion of a side wall that extends in the longer direction of the radiation surface 56 of the chassis 54. However, the present invention is not limited to the above configuration. The grip 54A may be disposed at other positions, for example, a central portion of a side wall extending in the shorter direction of the radiation surface 56 or a position biased by a distance in consideration of the position of the center of gravity of the electronic cassette 32 biased from central portion of the side wall.

In the imaging system 18 according to the exemplary embodiment, plural electronic cassettes 32, which have sizes corresponding to the spaces of the imaging portions of respective radiation images are prepared, and can be selectively used according to the imaging portions.

Note that, in the imaging system 18 according to the exemplary embodiment, two types of the electronic cassettes 32, i.e., a large electronic cassette 32 and a small electronic cassette 32 are applied as the plural electronic cassettes 32. The large electronic cassette 32 is used to perform imaging of a relatively wide area, such as a breast portion, an abdomen portion, and waist portion. The small electronic cassette 32 is used to perform imaging of a relatively small area, such as an arm portion and a leg portion. However, the present invention is not limited to the above. For Example, three types of electronic cassettes 32 can be applied according to the area and the imaging portions, or only one type of an electronic cassette 32 can be applied.

The power supplying apparatus 96 is prepared for each type of electronic cassette 32, namely, the large and the small electronic cassette 32, respectively. In order not to detract the portability of the electronic cassette 32 and to cope with the power consumed by the electronic cassette 32, the power supplying apparatus 96 for the large electronic cassette 32 is configured to be large, and the power supplying apparatus 96 for the small electronic cassette 32 is configured to be a small.

Figure 4:
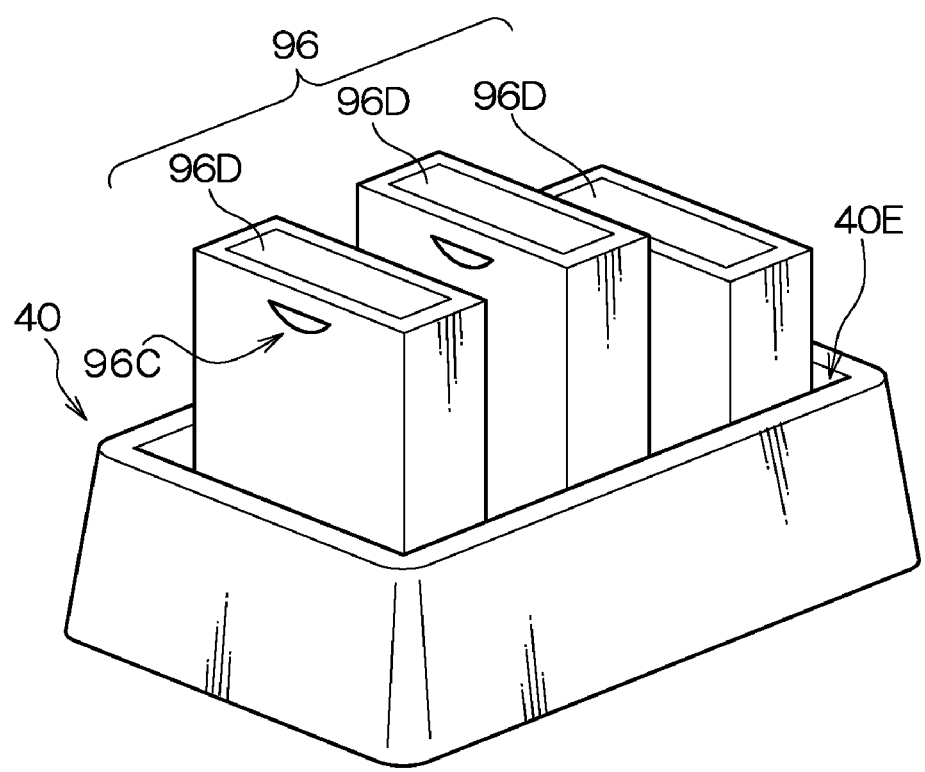
FIG. 4 is a perspective view showing configurations of a charging apparatus and a power supplying apparatus according to the exemplary embodiment of the present invention when the power supplying apparatus is mounted to the charging apparatus.

FIG. 4 shows a configuration of the charging apparatus 40 according to the exemplary embodiment.

The charging apparatus 40 can charge the above two types of the power supplying apparatus 96, namely, the large and the small power supplying apparatus 96. The charging apparatus 40 has an opening 40E disposed to its upper portion, in order to detachably mount the power supplying apparatuses 96. Note that, as shown in FIG. 4, the charging apparatus 40 according to the exemplary embodiment can charge two large power supplying apparatuses 96 and one small power supplying apparatus 96 at the same time. However, the present invention is not limited thereto. The types and the numbers of the power supplying apparatuses 96 that can be charged at the same time may be other combination.

Connectors (not shown) are disposed to the inner bottom surface of the charging apparatus 40 that electrically connects the power supplying apparatuses 96 when the power supplying apparatuses 96 is inserted from the opening 40E. The inserted power supplying apparatuses 96 are charged when the power supplying apparatus 96 are electrically connected to the connectors.

Further, lock mechanisms 40A, that individually fix (lock) the inserted power supplying apparatuses 96 to a predetermined charge positions (positions shown in FIG. 4), are disposed on an inner side wall of the charging apparatus 40 (refer to FIG. 6).

Further, the charging apparatus 40 is provided with a power supply section 40F (refer to FIG. 6) where power is supplied from a commercial power source. The power supply section 40F includes a communication port (for example, PoE (Power over Ethernet®) for communicating with the in-hospital network 16 through a power line of the commercial power source. Information passing through the communication port is transmitted to and from a memory access section 40D (refer to FIG. 6).

Note that, as shown in FIG. 4, recessed portion 96C is formed on the power supplying apparatus 96 to be hook when removing the power supplying apparatuses 96 from the charging apparatus 40. Accordingly, removing the power supplying apparatuses 96 can be performed easily by the recessed portions 96C.

The power supplying apparatus 96 according to the exemplary embodiment includes a display section 96D for displaying imaging order information (also refer to FIG. 7) and the like which will be described later. In the power supplying apparatus 96 according to the exemplary embodiment, a liquid crystal display is applied as the display section 96D, and visible display is performed. However, the invention is not limited thereto. Visible display by another displays, such as an organic EL display or a plasma display, or an audible indication by a sound playback apparatus or the like, may be applied as the display section 96D.

Figure 5A:
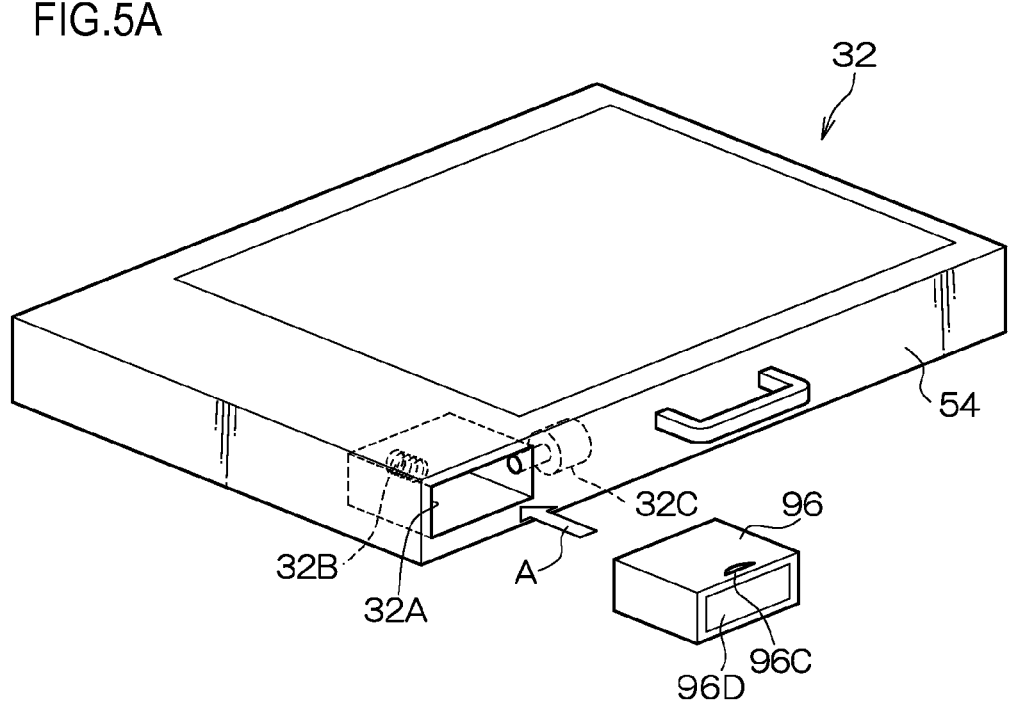
FIGS. 5A and 5B are perspective views showing an configuration of the electronic cassette according to the exemplary embodiment of the present invention when the power supplying apparatus is mounted detachably to the electronic cassette.

As shown in FIG. 5A, according to the exemplary embodiment, an opening 32A for mounting the power supplying apparatus 96 is formed in the vicinity of an end of the outside wall of the chassis 54 of the electronic cassette 32. Further, an urging member 32B is disposed to the deepest portion of the opening 32A to urge the power supplying apparatus 96 in a direction opposite to the direction in which the power supplying apparatus 96 is inserted (a direction an arrow A in FIG. 5A). Note that, in the electronic cassette 32 according to the exemplary embodiment, a spring is applied as the urging member 32B. However, the present invention is not limited to the spring, and a sheet spring, a solenoid, and the like, may be applied as the urging member.

A according to the exemplary embodiment, a connector (not shown) is disposed at the deepest portion of the electronic cassette 32 to electrically connect the power supplying apparatus 96 inserted from the opening 32A. The inserted power supplying apparatus 96 supplies the drive power to each power drive section of the electronic cassette 32 when the power supplying apparatus 96 is electrically connected to the connector.

Further, a fixing member 32C is disposed on an inner wall side of the opening 32A of the electronic cassette 32 to fix the inserted power supplying apparatus 96 to a position where the inserted power supplying apparatus 96 can be electrically connected to the connector. Note that, in the electronic cassette 32 according to the exemplary embodiment, a solenoid is applied as the fixing member 32C. However, the present invention is not limited to the solenoid, and other fixing member, which may fix the power supplying apparatus 96, may be applied.

Figure 5B:
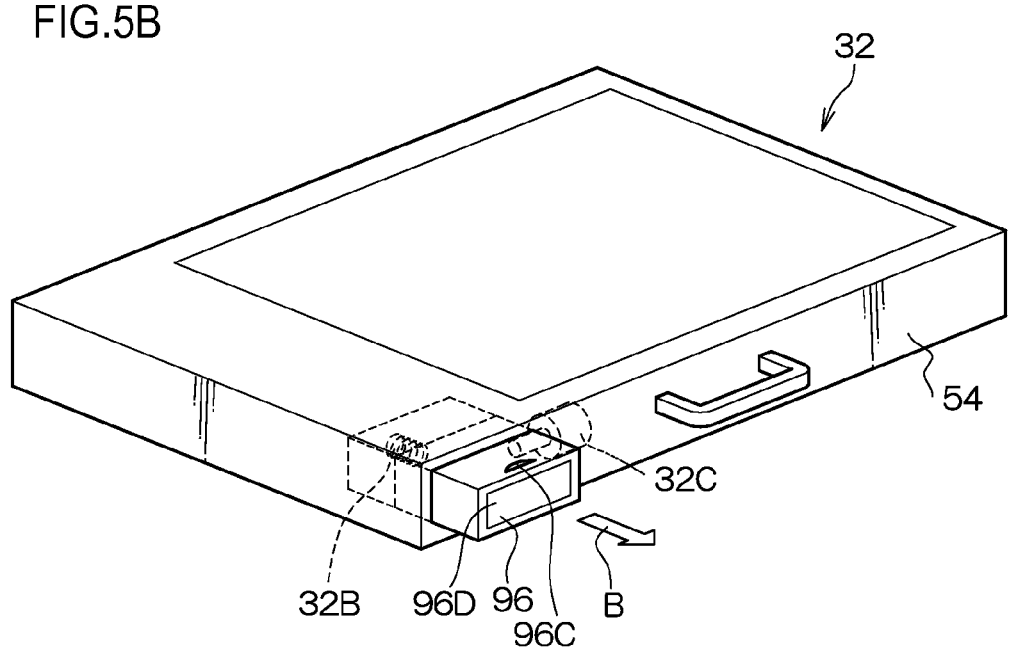

In the electronic cassette 32 according to the exemplary embodiment, when the power supplying apparatus 96 is inserted in the direction of the arrow A of FIG. 5A to the opening 32A as shown in FIG. 5A, and the power supplying apparatus 96 is fixed. The power supplying apparatus 96 is fixed in a manner that a plunger of the fixing member 32C composed of the solenoid is projected, and pushes a side surface of the power supplying apparatus 96 when the power supplying apparatus 96 is located at the position in which it is electrically connected to the connector. When the imaging has ended, the power supplying apparatus 96 is pushed in a direction of an arrow B of FIG. 5B by an urging force of the urging member 32B by retracting the plunger of the fixing member 32C, and therefore a part of the power supplying apparatus 96 projects from the electronic cassette 32 as shown in FIG. 5B. Accordingly, the user can easily remove the power supplying apparatus 96 from the electronic cassette 32 by drawing out the power supplying apparatus 96 by hooking a claw to the recessed portion 96C.

As described above, the power supplying apparatus 96 according to the exemplary embodiment is used when it is mounted to the electronic cassette 32 and the charging apparatus 40. Accordingly, it is preferred to provide the display section 96D on the power supplying apparatus 96 at a position where it can be visually seen in both case where the power supplying apparatus 96 is mounted to the electronic cassette 32 and case where the power supplying apparatus 96 is mounted to the charging apparatus 40. In the exemplary embodiment, the display section 96D is provided on a side face where the recessed portion 96C of the power supplying apparatus 96 is provided.

Next, main configuration of an electric system of the imaging system 18 according to the exemplary embodiment will be explained by referring to FIG. 6.

As shown in FIG. 6, a connection terminal 34A is disposed on the radiation generator 34 to communicate with the console 42. The console 42 is provided with a connection terminal 42A to communicate with the radiation generator 34. The connection terminal 34A of the radiation generator 34 is connected to the connection terminal 42A of the console 42 by a communication cable 35.

The radiation detector 60 contained in the electronic cassette 32 is arranged by layering a photoelectric conversion layer, that absorbs the radiation X and converts the radiation X to charges, within a TFT active matrix substrate 66. The photoelectric conversion layer is composed of amorphous selenium (a-Se) mainly consisting of, for example, selenium (for example, a content of 50% or more). When the photoelectric conversion layer is irradiated with the radiation X, the photoelectric conversion layer converts the irradiated radiation X to charges by generating amount of charges (pairs of electrons and holes) according to the amount of radiation irradiated therein. Note that, the radiation detector 60 may indirectly convert the radiation X to the charges by using a fluorescent material and a photoelectric conversion device (photodiode) in place of the radiation/charges conversion material that directly converts the radiation X to the charges. Gadolinium sulphur dioxide (GOS) and cesium iodide (CsI) are well known as the fluorescent material. In this case, radiation X is converted to light by the fluorescent material, and light is converted to charges by a photodiode of the photoelectric conversion device.

Further, plural storage capacitors 68 and plural pixel sections 74 (Note that, in FIG. 6, the photoelectric conversion layers corresponding to each pixel section 74 are schematically shown as photoelectric conversion sections 72) are disposed on the TFT active matrix substrate 66 in matrix. The storage capacitors 68 store the charges generated by the photoelectric conversion layers. The pixel sections 74 include TFTs 70 for reading out the charges stored to the storage capacitors 68. The charges, generated in the photoelectric conversion layers by irradiating the radiation X to the electronic cassette 32, are stored into the storage capacitors 68 of each pixel section 74. With this operation, the image information, which is carried by the radiation X irradiated to the electronic cassette 32, is converted to charge information and held by the radiation detector 60.

Further, the TFT active matrix substrate 66 is provided with plural gate lines 76 and plural data lines 78. The plural gate lines 76 extend in a predetermined direction (row direction) and turns on and off the TFTs 70 of each pixel section 74. The plural data lines 78 extend in a direction (column direction) orthogonal to the gate lines 76 and reads out the stored charges from the storage capacitors 68 through the turned on TFTs 70. Each of The gate line 76 is connected to a gate line driver 80. Further, each of the data line 78 is connected to a signal processing section 82. When charges are stored into the storage capacitors 68 of each of the pixel section 74, the TFTs 70 of the respective pixel sections 74 are sequentially turned on in a row in response to signals supplied from the gate line driver 80 via the gate lines 76. Further, the charges, which are stored in the storage capacitors 68 of the pixel sections 74 whose TFTs 70 are turned on, are transmitted to the data lines 78 as analog electric signals, and input into the signal processing section 82. Accordingly, the charges stored in the storage capacitors 68 of the respective pixel sections 74 are sequentially read out in the row section.

The signal processing section 82 includes amplifiers (not shown) and sample hold circuits (not shown) disposed in each of the data lines 78. The charge signals, transmitted via the data lines 78, are held by the sample hold circuits after being amplified by the amplifiers. Further, multiplexers and A/D (analog/digital) converters are sequentially connected to the output side of the sample hold circuits. The charge signals held by the respective sample hold circuits are sequentially (serially) input to the multiplexers and are converted to digital image data by the A/D converters.

An image memory 90 is connected to the signal processing section 82. The image data output from the A/D converters of the signal processing section 82 is sequentially stored to the image memory 90. The image memory 90 has a storage capacity that stores plural number (in the exemplary embodiment, six) of image data. Each time a radiation image is imaged, the image data obtained by the imaging are sequentially stored in the image memory 90.

The image memory 90 is connected to a cassette controller 92 that overall controls the operation of the electronic cassette 32. The cassette controller 92 includes a microcomputer including a CPU (central processing section) 92A, a memory 92B having a ROM and a RAM, and a non-volatile storage section 92C configured by a HDD, a flash memory, or the like.

Further, the cassette controller 92 is connected to a wireless communication section 94. The wireless communication section 94 follows the wireless LAN (Local Area Network) standards such as IEEE (Institute of Electrical and Electronics Engineers) 802.11 a/b/g, or the like. The wireless communication section 94 controls transmission of various information to external equipments via the wireless communication. The cassette controller 92 can wirelessly communicate with the console 42 via the wireless communication section 94. Further, the cassette controller 92 can transmit and receive various information to and from the console 42. The cassette controller 92 stores an exposure condition received from the console 42 via the wireless communication section 94 and starts to read out the charges based on the exposure condition.

Further, the power supplying apparatus 96 is connected to the cassette controller 92 when the power supplying apparatus 96 is fixed by the fixing member 32C (also refer to FIG. 5A and FIG. 5B).

The power supplying apparatus 96 according to the exemplary embodiment is provided with a secondary battery (hereinafter, called a "battery") 96A, a memory 96B, and the above described display section 96D. The battery, which is rechargeable, supplies drive power to each of the power drive section of the electronic cassette 32. The memory 96B stores therein the image data obtained by imaging and various information, such as the imaging order information. Note that, in the power supplying apparatus 96 according to the exemplary embodiment, a non-volatile and rewritable memory (a flash memory in the exemplary embodiment) is applied as the memory 96B. However, the present invention is not limited to the flash memory, and a volatile memory such as a RAM may be applied, and the battery 96A may be used as a back-up power supply of the memory 96B. Further, in the power supplying apparatus 96 according to the exemplary embodiment, a nickel cadmium battery is applied as the battery 96A. However, the present invention is not limited thereto, and other secondary batteries such as a nickel hydride battery or a lithium ion battery may be applied.

Various circuits and devices (the gate line driver 80, the signal processing section 82, the image memory 90, the wireless communication section 94, the microcomputer acting as the cassette controller 92, and the like) described above of the electronic cassette 32 according to the exemplary embodiment, are operated by the power supplied from the battery 96A of the power supplying apparatus 96 when the power supplying apparatus 96 is mounted. Further, the cassette controller 92 can access the memory 96B of the power supplying apparatus 96 when the power supplying apparatus 96 is mounted the electronic cassette 32. Together therewith, the cassette controller 92 controls the display section 96D to display various information thereon. Note that, in FIG. 6, wirings for connecting the power supplying apparatus 96 to the various circuits and devices are omitted.

On the other hand, the console 42 is configured as a server computer. The console 42 includes a display 100 and an operation panel 102. The display 100 displays an operation menu, an imaged radiation image, and the like. The operation panel 102 has plural keys, and various information and operating instructions are inputted through the operation panel 102.

Further, the console 42 according to the exemplary embodiment includes a CPU 104, a ROM 106, a RAM 108, a HDD 110, a display driver 112, and an operation input detector 114. The CPU 104 controls the overall apparatus. The ROM 106 previously stores various programs including a control program, and the like. The RAM 108 temporarily stores various data. Further, the HDD 110 temporarily stores various data. The display driver 112 controls to display various information on the display 100. The operation input detector 114 detects operation state inputted form the operation panel 102. Further, the console 42 includes a communication interface (I/F) section 116, a wireless communication section 118, and a charging apparatus controller 120. The communication interface (I/F) section 116, connected to the connection terminal 42A, transmits and receives various information, such as the exposure condition and the like, to and from the radiation generator 34 via the connection terminal 42A and the communication cable 35. The wireless communication section 118 transmits and receives various information, such as the exposure condition, the image data, and the like, to and from the electronic cassette 32 by wireless communication. The charging apparatus controller 120 controls the operation of the charging apparatus 40.

The CPU 104, the ROM 106, the RAM 108, the HDD 110, the display driver 112, the operation input detector 114, the communication I/F section 116, the wireless communication section 118, and the charging apparatus controller 120 are mutually connected together therewith through a system bus BUS. Accordingly, the CPU 104 may access the ROM 106, the RAM 108, and the HDD 110. In addition to the above operation, the CPU 104 can control to display various information on the display 100 through the display driver 112, transmit and a receipt various information to and from the radiation generator 34 via the communication I/F section 116, and transmit and a receipt various information to and from the electronic cassette 32 via the wireless communication section 118. Further, the CPU 104 can recognize an operation state of the user's operation to the operation panel 102, through the operation input detector 114.

The charging apparatus controller 120 is connected to the charging apparatus 40 via the communication cable 18. The CPU 104 may control the operations of the respective sections, such as the lock mechanisms 40A, in the charging apparatus 40 via the charging apparatus controller 120.

According to the exemplary embodiment, the charging apparatus 40 includes a display controller 40B for controlling the display section 96D provided in the power supplying apparatus 96. The CPU 104 controls the display section 96D to display various information on the display section 96D via the charging apparatus controller 120 and the display controller 40B.

The charging apparatus 40 according to the exemplary embodiment includes a charging section 40C for charging the battery 96A disposed in the power supplying apparatus 96. The CPU 104 controls the charging to the battery 96A via the charging apparatus controller 120 and the charging section 40C.

Further, the charging apparatus 40 according to the exemplary embodiment includes a memory access section (hereinafter, called "an access section") 40D for accessing the memory 96B disposed in the mounted power supplying apparatus 96, and the CPU 104 controls the access to the memory 96B via the charging apparatus controller 120 and the access section 40D.

The radiation generator 34 includes a radiation source 130, a communication I/F section 132, and a radiation source controller 134. The radiation source 130 emits the radiation X. The communication I/F section 132 transmits and receives various information, such as the exposure condition, to and from the console 42. The radiation source controller 134 controls the radiation source 130 based on the received exposure condition.

The radiation source controller 134 is configured by a microcomputer and stores the received exposure condition and the posture information. The exposure condition includes information such as a tube voltage, a tube current, and an irradiation period. The radiation source controller 134 causes the radiation source 130 to radiate the radiation X based on the received exposure condition.

Namely, in the imaging system 18 according to the exemplary embodiment, patients to whom radiation imaging is performed are accepted in the imaging management rooms established in each of the radiation imaging room 44 as described above. Each of the radiation imaging room 44 keeps the information of the patients to whom the radiation imaging is performed, as imaging order information. Next, in each of the radiation imaging room 44, the radiation imaging is performed to each of the patients, based on the imaging order information.

The console 42 disposed to the imaging management room of each of the radiation imaging room 44 obtains the patient information and the imaging menu, included in the database 14A, from the RIS server 14, and stores the patient information and the imaging menu in the HDD 110 as the imaging order information. Then, the console 42 controls the electronic cassette 32, the radiation generator 34, and the charging apparatus 40 based on the imaging order information.

Figure 7:
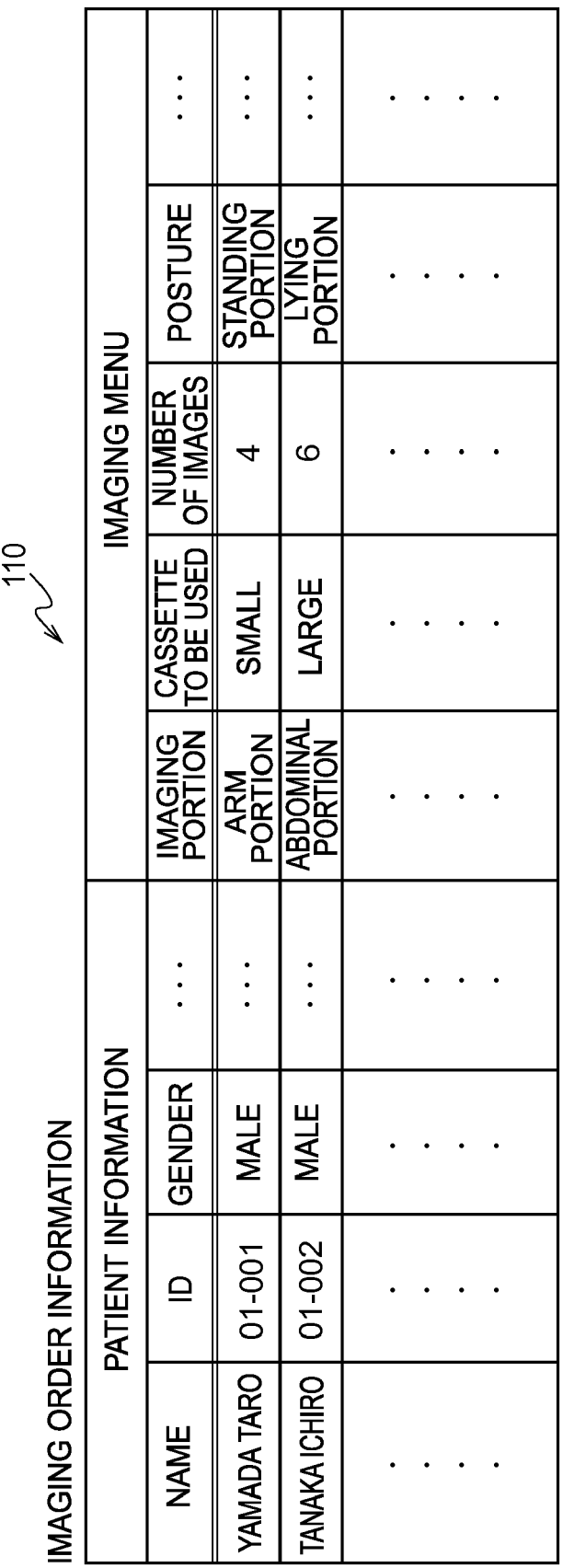
FIG. 7 is a schematic view showing a configuration of imaging order information according to the exemplary embodiment of the present invention.

FIG. 7 schematically shows the imaging order information according to the exemplary embodiment.

As shown in FIG. 7, the imaging order information according to the exemplary embodiment is configured as a combination of patient information of a patient whose imaging is planed, such as name, ID, and gender, and an imaging menu associated with the radiation imaging of the corresponding patient, such as the imaging portion, the cassette to be used, number of images to be imaged, and the posture.

The imaging order information shown in FIG. 7 stores information indicating, for example, ID of "Taro Yamada" as "01-001", his gender as "male", the imaging portion as "an arm portion", an electronic cassette 32 to be used in imaging as a small electronic cassette, the number of images to be imaged as four, and the posture of the patient as "a standing position".

Next, operation of the imaging system 18 according to the exemplary embodiment will be explained. Note that, to avoid complexity, a case where the imaging order information is stored in the HDD 110 will be explained.

First, a patient to whom radiation imaging is performed (hereinafter, called "an examinee") is accepted at a reception table of an imaging management room of a radiation imaging room 44 in which the radiation imaging is performed to the examinee.

A receptionist at the reception table inputs information (in the exemplary embodiment, the name of the examinee) showing the accepted examinee to the console 42 installed at the imaging management room through the operation panel 102. Thereafter, the receptionist inputs an instruction for executing an examinee information writing process through the operation panel 102.

Figure 8:
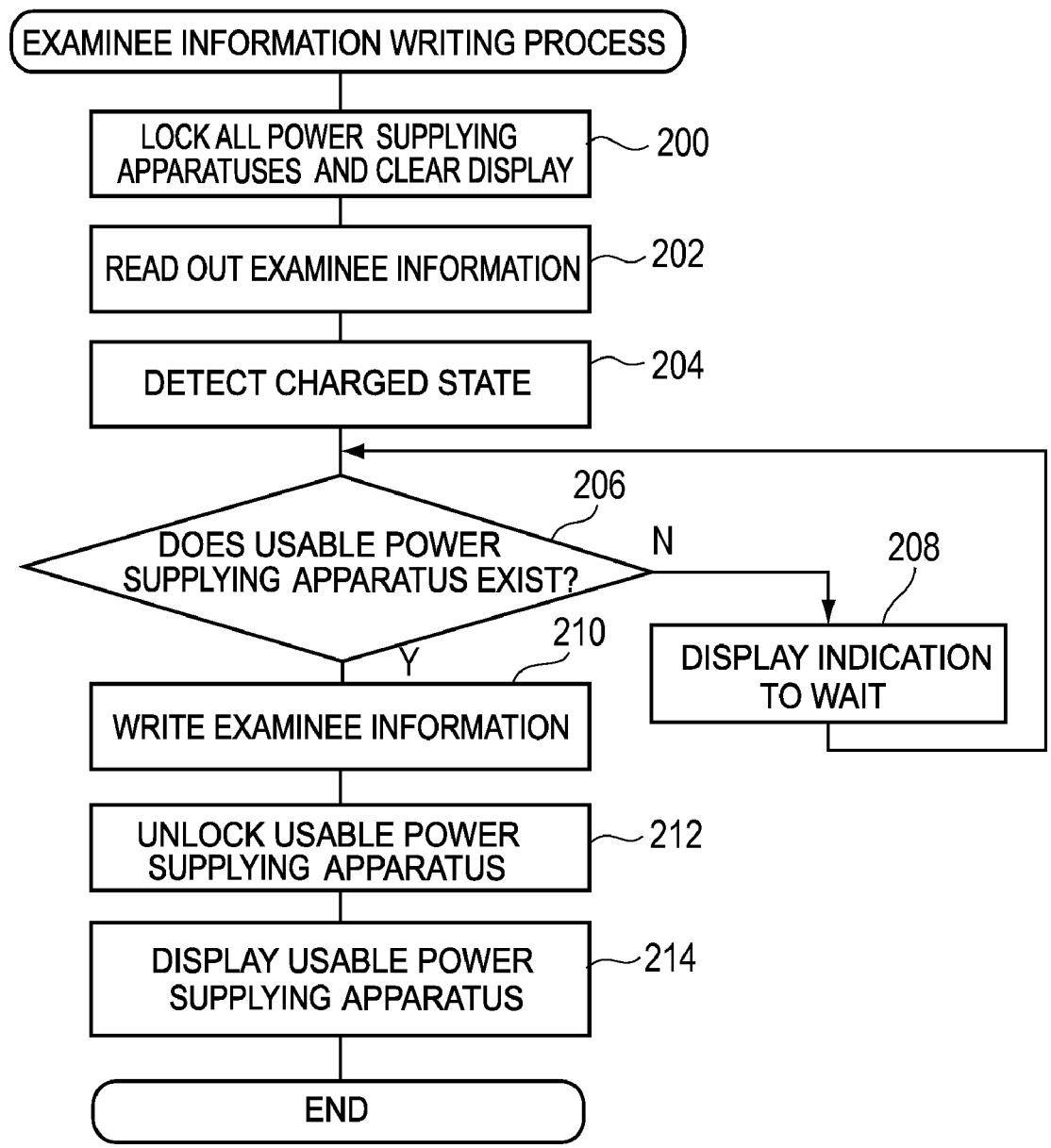
FIG. 8 is a flowchart showing a process of an examinee information writing process program according to the exemplary embodiment of the present invention.

Next, operation of the console 42 when the examinee information writing process is executed will be explained by referring to FIG. 8. Note that FIG. 8 is a flowchart showing a flow of process of examinee information writing process program executed by the CPU 104 of the console 42. The program is previously stored to a predetermined region of the ROM 106.

In step 200 of FIG. 8, all the mounted power supplying apparatuses 96 are fixed (locked) by the lock mechanisms 40B. Next, in step 200 of FIG. 8, the charging apparatus controller 120 controls the charging apparatus 40 connected to the power supplying apparatuses 96. By this process, all the power supplying apparatuses 96 mounted to the charging apparatus 40 can not be removed.

Further, in step 200, the charging apparatus 40 is controlled, via the charging apparatus controller 120 and the display controller 40B, so that all of the display sections 96D in all of the power supplying apparatus 96 mounted to the charging apparatus do not display any information.

In next step 202, the information associated with the examinee (hereinafter, called "examinee information") accepted in the reception table, which is included in the imaging order information (also refer to FIG. 7), is read out from the HDD 110. In next step 204, all of the charge amounts of the power supplying apparatuses 96 mounted to the charging apparatus 40 are detected through the charging apparatus controller 120 and the charging section 40C.

In next step 206, a power supplying apparatus 96 corresponding to an electronic cassette 32 used for the radiation imaging of the examinee, is specified based on the information of the examinee read out in the process of step 202. Next, it is determined whether a power supplying apparatus 96, which can be used for the radiation imaging of the examinee, exists in the charging apparatus 40, based on the charged amount of each of the power supplying apparatuses 96 obtained by the process in step 204 and based on the examinee information. When the determination is made negative, the process proceeds to step 208. At step 208, the display driver 112 is controlled to cause the display 100 to show information indicating to wait because no usable power supplying apparatus 96 exists. Thereafter, the process returns to step 206. On the other hand, when the determination made is affirmative, the process proceeds to step 210.

Note that, the type of the power supplying apparatus 96, which can be used for each type of electronic cassette 32, is predetermined (in the exemplary embodiment, the large power supplying apparatus 96 is used for the large electronic cassette 32 and the small power supplying apparatus 96 is used for the small electronic cassette 32). Therefore, the console 42 refers to "usable cassette" in the imaging menu included in the examinee information. With this operation, the console 42 may uniquely specify the power supplying apparatus 96 corresponding to the electronic cassette 32 which is shown by the "usable cassette" to be used for the radiation imaging of the examinee.

The determination whether the power supplying apparatus 96, which can be used for the radiation imaging of the examinee, exists in the charging apparatus 40 is performed by determining whether the same type of the power supplying apparatus 96 as that of the specified power supplying apparatus 96 is mounted to the charging apparatus 40. Further, determination whether a capable power supplying apparatus 96, which may be used for the radiation imaging, exists is performed by determining whether the charged amount of the power supplying apparatus 96 has reached the charge amount for radiation imaging of the number of images, required by "number of images" in the imaging menu included in examinee information.

In step 210, via the charging apparatus controller 120 and the access section 40D, the examinee information is written in the memory 96B provided in the power supplying apparatus 96 which has been determined to be used in the step 206 (hereinafter, called "usable power supplying apparatus"). Next, in step 212, the charging apparatus 40 is controlled, via the charging apparatus controller 120 and the display controller 40B, to display the examinee information written in the memory 96B by the display section 96D provided in the usable power supplying apparatus. By this process, as shown in FIG. 9 as an example, the examinee information is displayed on the display section 96D of the usable power supplying apparatus. Note that, FIG. 9 illustrates a state where the examinee in the imaging order information shown in FIG. 7 is "Taro Yamada".

In next step 214, the charging apparatus 40 is controlled through the charging apparatus controller 120 to cause a lock mechanism 40A corresponding to the usable power supplying apparatus 96 to be released. Accordingly, the only usable power supplying apparatus can be removed from the charging apparatus 40. Thereafter, the examinee information writing process program is ended.

The receptionist detaches, the power supplying apparatus 96, which the examinee information is displayed on the display section 96D, from the charging apparatus 40 and hands it to the examinee as the usable power supplying apparatus.

The examinee enters the radiation imaging room 44 carrying the usable power supplying apparatus passed to him or her from the receptionist. Next, the examinee passes the usable power supplying apparatus to a radiological technologist or a doctor (hereinafter, called "radiological technologist") waiting in the radiation imaging room 44.

The radiological technologist mounts the usable power supplying apparatus passed from examinee on the corresponding electronic cassette 32, and thereafter, the imaging menu associated with the examinee, included in the imaging order information stored to the HDD 110, is displayed on the display 100. Next, the radiological technologist performs an exposure condition specifying operation, that specifies the tube voltage, the tube current, and the irradiation period of the radiation X when irradiated, through the operation panel 102 of the console 42, based on the imaging condition, such as an imaging portion of the examinee and the number of images to be imaged, which can be found in the imaging menu.

At this time, while showing the examinee the display section 96D of the usable power supplying apparatus, the radiological technologist reads out the name included in the examinee information displayed on the display section 96D, like "Are you Mr. Taro Yamada?". Due thereto, the radiological technologist can confirm that the name displayed on the display section 96D matches with the name of the examinee. Accordingly, the exemplary embodiment of the present invention can prevent a situation where the examinee is not subject how is planed to be imaged (misidentification of the imaging subject).

On the other hand, when the usable power supplying apparatus is mounted to the electronic cassette 32, the electronic cassette 32 reads out the examinee information from the memory 96B disposed in the usable power supplying apparatus, and transmits the examinee information to the console 42 by wireless communication.

When the console 42 receives the examinee information from the electronic cassette 32, the console 42 performs a radiation image imaging process.

Figure 10:
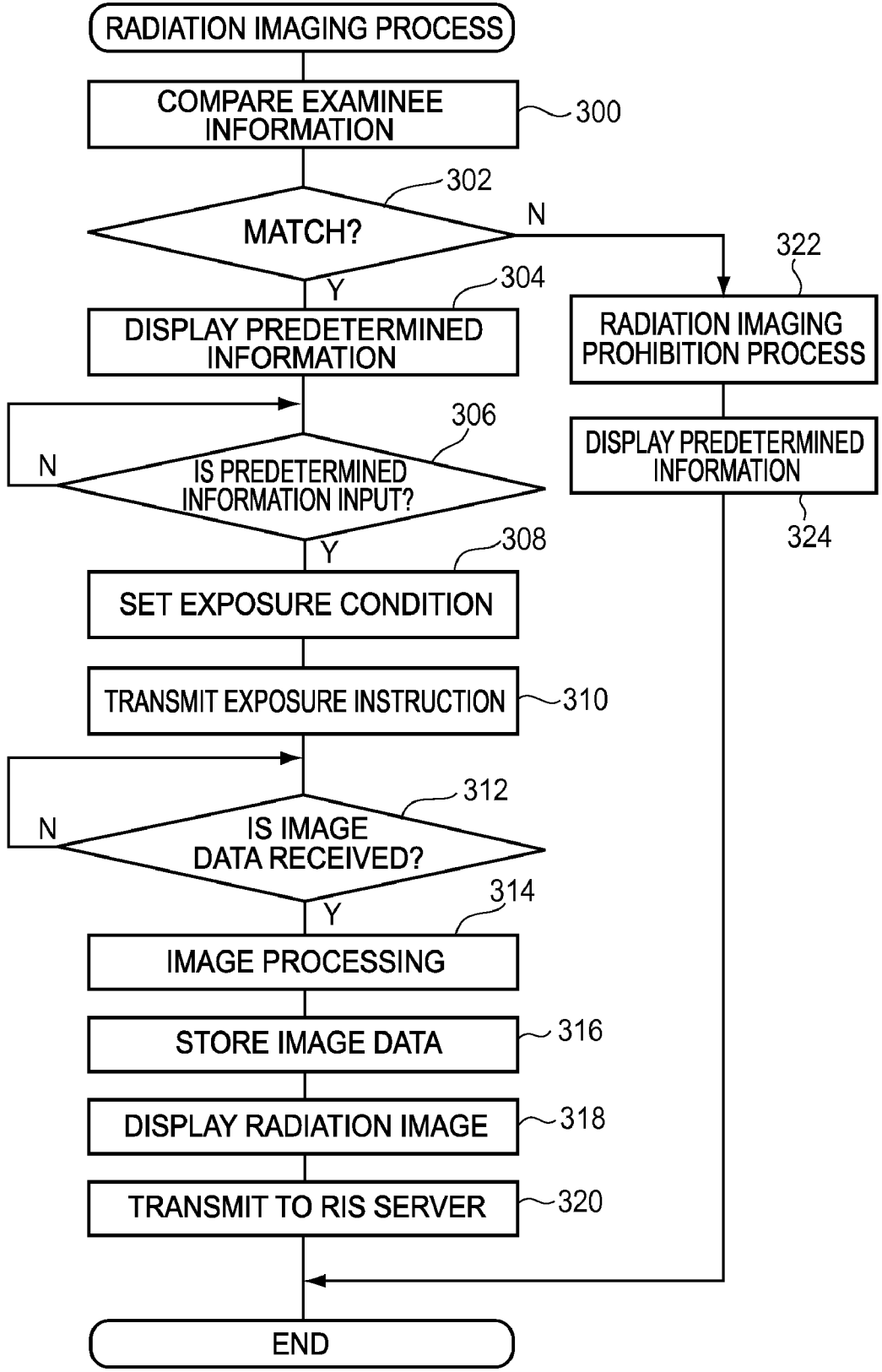
FIG. 10 is a flowchart showing the flow of processes of the radiation imaging process program according to the exemplary embodiment.

Next, operation of the console 42 when the examinee information writing process is performed will be explained by referring to FIG. 10. Note that, FIG. 10 is a flowchart showing a flow of process of the examinee information writing process program, executed by the CPU 104 of the console 42. The radiation imaging process program is previously stored in the predetermined region of the ROM 106.

In step 300 of FIG. 10, the examinee information received from the electronic cassette 32 is compared with the imaging order information stored in the HDD 110 (also refer to FIG. 7). In next step 302, it is determined whether information that matches with the received examinee information is included in the imaging order information. When the determination is affirmative, the process proceeds to step 304. At step 304, the display driver 112 is controlled to cause the display 100 to display predetermined information showing that imaging is permitted. Thereafter, in next step 306, an input of predetermined information is waited.

Figure 11A:
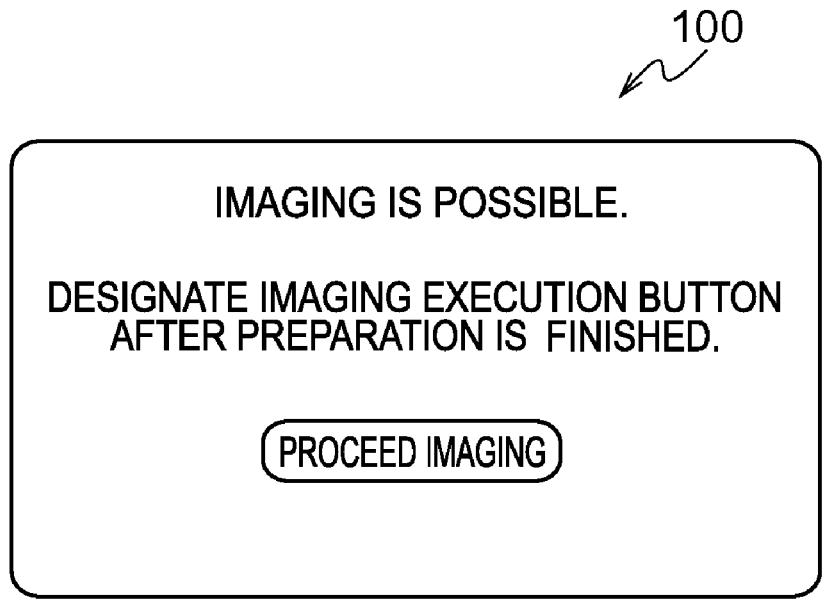
FIG. 11A and FIG. 11B are schematic views showing an example of an information displayed when the radiation imaging process program according to the exemplary embodiment of the present invention is executed.

FIG. 11A shows an example of information displayed on the display 100 by the process of step 304. In the example shown in FIG. 11A, a message "imaging is possible, designate imaging execution button after a predetermined preparation is performed" is displayed on the display 100 together with the imaging execution button.

When the information as shown in FIG. 11A is displayed on the display 100, the radiological technologist guides the examinee to lie at the imaging position 50 in the upper space of the bed 46 or to stand at the imaging position 48 in the front space of the rack 45, according to the posture (the lying position or the standing position) of the examinee when imaging, which is shown in the imaging menu displayed on the display 100.

Next, the radiological technologist disposes the electronic cassette 32 between a floor surface of the bed 46 and the imaging portion, or disposes the electronic cassette 32 at a position in a height direction of the rack 45, according to the imaging portion.

Next, the radiological technologist operates the supporting/moving mechanism 52 to dispose the radiation generator 34 in front of the imaging portion. Thereafter, the radiological technologist designates the imaging execution button displayed on the display 100. Accordingly, the determination of step 306 becomes affirmative in response to the designation, and the process proceeds to step 308.

In step 308, the exposure condition is set by transmitting the designated exposure condition to the radiation generator 34 and the electronic cassette 32. Accordingly, the radiation source controller 134 prepares to expose based on the received exposure condition in response to the set exposure condition.

In next step 310, instruction information for instructing a start of exposure is transmitted to the radiation generator 34 and the electronic cassette 32.

In response to the instruction information, the radiation source 130 generates and irradiates the radiation based on the tube voltage, the tube current, and the irradiation period, according to the exposure condition received by the radiation generator 34 from the console 42.

The radiation X irradiated from the radiation source 130 reaches the electronic cassette 32 after passing through the examinee. With this operation, charges are stored in the storage capacitors 68 of each of the pixel section 74 of the radiation detector 60 contained in the electronic cassette 32.

The cassette controller 92 of the electronic cassette 32 controls the gate line driver 80 after the irradiation period designated by the exposure condition has passed, after the cassette controller 92 receives the instruction information instructing the start of exposure. The control is performed by causing the gate line driver 80 to output on-signals sequentially to each of the gate line 76 and to turn on sequentially each of the TFT 70 connected to each of the respective gate line 76.

When each of the TFT 70 connected to each of the gate lines 76 are turned on sequentially through each line, the charges, which are stored in each of the storage capacitor 68, flow out through the respective data lines 78 as electric signals. The electronic signals flown out through the respective data lines 78 are converted to digital image data by the signal processing section 82 and are stored in the image memory 90.

After the completion of the imaging, the cassette controller 92 reads out the image data stored in the image memory 90 and stores (transfers) the image data to the memory 96B of the power supplying apparatus 96.

On the other hand, on the completion of the imaging, the radiological technologist removes the power supplying apparatus 96 from the electronic cassette 32 and passes the power supplying apparatus 96 to the examinee.

The examinee carries the power supplying apparatus 96 passed to him or her, and passes it to the receptionist at the reception table.

When the receptionist receives the power supplying apparatus 96 from the examinee, the receptionist mounts the power supplying apparatus 96 to corresponding position of the charging apparatus 40.

When the power supplying apparatus 96 is mounted to the charging apparatus 40, the charging apparatus 40 starts to charge the battery 96A disposed on the power supplying apparatus 96 by the charge section 40C, reads out the image data from the memory 96B through the access section 40D, and transmits the image data to the console 42.

In next step 312, the process waits until the image data is received from the charging apparatus 40. In next step 314, an image process for performing various corrections, such as a shading correction, is executed to the received image data.

In next step 316, the image data subjected to the image process (hereinafter, called "corrected image data") is stored to the HDD 110. In next step 318, the display driver 112 is controlled to cause the display 100 to display a radiation image shown by the corrected image data for confirmation and the like. In next step 320, after the corrected image data is transmitted to the RIS server 14 via the in-hospital network 16, the radiation imaging process program is ended. Note that, the corrected image data transmitted to the RIS server 14 is then stored in the database 14A and permits the doctor to read and diagnose the radiation image.

On the other hand, when the determination becomes negative in step 302, the process proceeds to step 322. In step 322, a predetermined process, that inhibits the imaging of radiation image (hereinafter, called "radiation imaging inhibition process") is executed. Note that, the radiation imaging process program applies a process, which transmits instruction information that forcibly shuts off a supply path of the drive power to the radiation source 130 of the radiation generator 34. However, the present invention is not limited to the process, and it is needless to say that other process capable of inhibiting imaging of a radiation image, for example, a process for transmitting instruction information for stopping an operation of the power supplying apparatus 96 to the electronic cassette 32, and the like may be applied.

In next step 324, the display driver 112 is controlled to cause the display 100 to display a predetermined information showing that an examinee to whom radiation imaging is planed to be performed can be an examinee whose radiation imaging is not planed (the former patient may be misidentified with the latter patient). Thereafter, the radiation imaging processing program is ended.

Figure 11B:
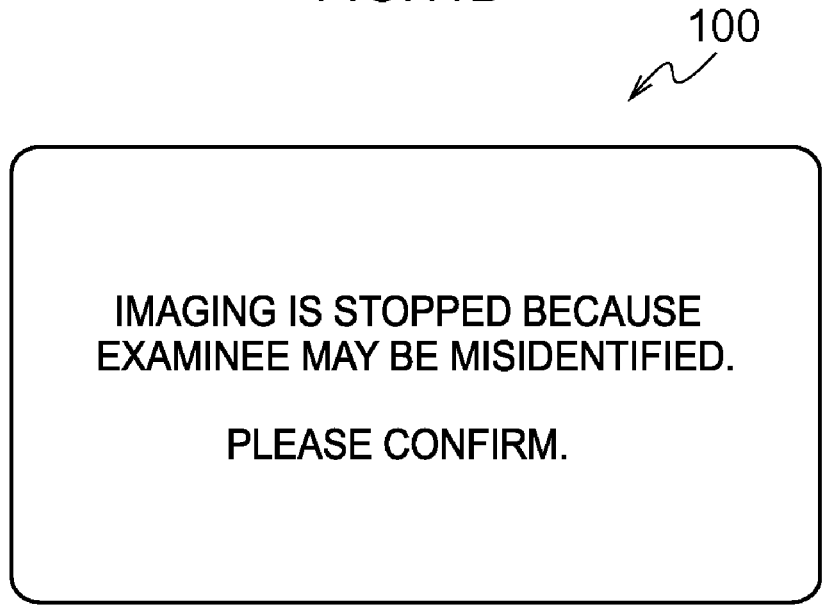

FIG. 11B shows an example of the information displayed on the display 100 by the process of step 324. In the example of FIG. 11B, message is displayed indicating that "imaging is stopped because an examinee may be misidentified, thus please make confirmation". Accordingly, by referring to the information, the radiological technologist may easily find out that an examinee may be misidentified, and that imaging has been stopped.

As explained above in detail, in the exemplary embodiment, the power supplying apparatus (in the exemplary embodiment, the power supplying apparatus 96), which is mounted detachably to the radiation imaging apparatus (in the exemplary embodiment, the electronic cassette 32), includes the display section (in the exemplary embodiment, the a display section 96D) for displaying the imaging subject information (in the exemplary embodiment, the examinee information) associated with the imaging subject. Accordingly, the exemplary embodiment can prevent misidentification of the imaging subject without requiring a large-scale configuration.

In the exemplary embodiment, the power supplying apparatus includes a storing section (the memory 96B) that stores the imaging subject information. Further, in the exemplary embodiment, the display section 96D displays the imaging subject information stored in the storing section. Therefore, in the exemplary embodiment, the power supplying apparatus 96 can hold the imaging subject information. Accordingly, the exemplary embodiment of the present invention can improve the convenience for the user.

Further, the exemplary embodiment includes the charging apparatus (in the exemplary embodiment, the charging apparatus 40) provided with the charging section (in the exemplary embodiment, the charging section 40C) for charging the power supply section (in the exemplary embodiment, the battery 96A) of the power supplying apparatus when the power supplying apparatus is mounted, and is provided with the writing section (in the exemplary embodiment, the access section 40D) for writing the imaging subject information in the storage section of the power supplying apparatus when the power supplying apparatus is mounted, before the power supplying apparatus is mounted to the radiation imaging apparatus. Accordingly, in the exemplary embodiment, the imaging subject information can be simply written to the storage section of the power supplying apparatus. As a result, the exemplary embodiment can simply prevent the misidentification of the imaging subject.

In particular, according to the exemplary embodiment, the storage section of the power supplying apparatus further stores the image information (in the exemplary embodiment, the image data) obtained by the imaging performed by the radiation imaging apparatus, and the charging apparatus includes the reading section (in the exemplary embodiment, access portion 40D) for reading the image information stored in the storage section when the power supplying apparatus is mounted. Accordingly, the exemplary embodiment can transfer the image information obtained by the imaging performed to the higher-level devices via the charging apparatus. Therefore, the exemplary embodiment can more securely perform the transfer when compared with a case where the transfer is performed wirelessly.

Further, the exemplary embodiment includes a communication port that connects the power supply section 40F to the in-hospital network 16. Accordingly, in the exemplary embodiment, the communication port realizes the charging apparatus 40 to be installed to any location that has a supply section (outlet) of the commercial power source. As a result, the exemplary embodiment can realize a more reliable prevention of misidentification.

Further, in the exemplary embodiment, the radiation imaging apparatus includes the transmission section (in the exemplary embodiment, the wireless communication section 94) for transmitting the imaging subject information stored in the storage section when the power supplying apparatus is mounted before the imaging subject corresponding to the imaging subject information is imaged. Further, the exemplary embodiment includes the receiving section (in the exemplary embodiment, the wireless communication section 118) for receiving the transmitted imaging subject information, the determination section (in the exemplary embodiment, the CPU 104) for determining whether the received imaging subject information is the information corresponding to the imaging subject, and the process execution section (in the exemplary embodiment, the CPU 104) for executing a predetermined process based on a result of determination determined by the determination section. Thus, the exemplary embodiment can perform a process according to the result of determination whether a person, who is the imaging subject of the imaging, is a person whose imaging is planned. Accordingly, the exemplary embodiment can prevent the misidentification of the imaging subject on a higher level.

In particular, in the exemplary embodiment, when it is determined that the imaging subject information is not the information that corresponds to the imaging subject, as the result of determination, the process execution section executes the process for inhibiting imaging of the imaging subject as the predetermined process. Accordingly, the exemplary embodiment may more securely prevent the misidentification of the imaging subject.

Further, the exemplary embodiment determines, by the determination section, whether the received imaging subject information matches with the imaging subject information written by the writing section. Accordingly, the present exemplary embodiment of the present invention, determines whether the received imaging subject information is the information that corresponds to the imaging subject to be imaged. Therefore, the exemplary embodiment can more securely prevent the misidentification of the imaging subject.

Further, in the exemplary embodiment, the imaging subject information includes the specific information (in the exemplary embodiment, the patient information) for specifying the imaging subject. Accordingly, the exemplary embodiment can confirm the imaging subject in a simplified manner. As a result, the exemplary embodiment can prevent the misidentification of the imaging subject in a simplified manner.

In particular, in the exemplary embodiment, the imaging subject information further includes the information (in the exemplary embodiment, the imaging menu) showing the imaging condition to the imaging subject. Accordingly, the exemplary embodiment may perform various processes using the information. As a result, the exemplary embodiment can improve the convenience of the user.

Further, in the exemplary embodiment, the charging apparatus includes the detachment inhibition section (in the exemplary embodiment, the lock mechanisms 40A) for inhibiting to detachment of the power supplying apparatus when the power supply section of the power supplying apparatus has not been charged when the charging apparatus is attached to the power supplying apparatus. Accordingly, the exemplary embodiment may previously prevent to use the power supplying apparatus which has not been charged. As a result, the exemplary embodiment can improve the convenience of the user.

Further, in the exemplary embodiment, the radiation imaging apparatus is arranged as the electronic cassette. Accordingly, the exemplary embodiment can prevent the misidentification of the imaging subject without a large-scale configuration.

In the above, the present invention has been explained based on the exemplary embodiment. However, the technical scope of the present invention is not limited to the scope described in the exemplary embodiment. The exemplary embodiment may be added with various changes and improvements within a scope which does not depart from the gist of the present invention. Further, in the exemplary embodiments, changes and modifications that can be added are also included in the technical scope of the present invention.

Further, the exemplary embodiment does not limit the inventions recited in the claims. Further, all the combinations of the features explained in the exemplary embodiment are not always indispensable to embody the present invention. Since the exemplary embodiment described above includes inventions at various steps, various inventions may be extracted by appropriately combining plural disclosed components. As long as an advantage may be obtained even if some components are deleted from all the components disclosed in the exemplary embodiment, the configuration from which the some components are deleted may be extracted as the present invention.

For example, the exemplary embodiment has been explained with a case where both the examinee information writing process program (refer to FIG. 8) and the radiation imaging process program (refer to FIG. 10) are executed by the console 42. However, the present invention is not limited thereto. For example, one of the examinee information writing process program or the radiation imaging process program may be executed by the charging apparatus 40, as an alternative exemplary embodiment. In this case, the charging apparatus 40 is provided with a controller, and one of the programs is executed by the controller. The same advantage as that of the above exemplary embodiment may be achieved in this case.

Further, in the exemplary embodiment, FIGS. 5A and 5B shows an example of a mode of the electronic cassette. However, the present invention is not limited thereto. For example, the present invention may be arranged as shown in FIG. 12A and FIG. 12B.

Figure 12A:
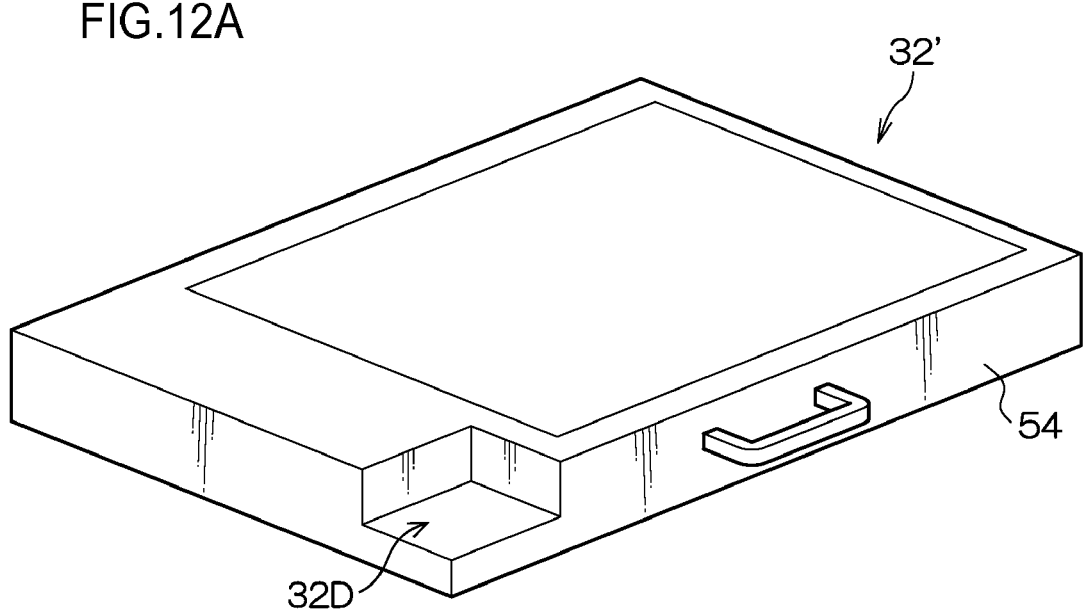
FIG. 12A and FIG. 12B are perspective views showing a modification of an electronic cassette according to another exemplary embodiment of the present invention.
Figure 12B:
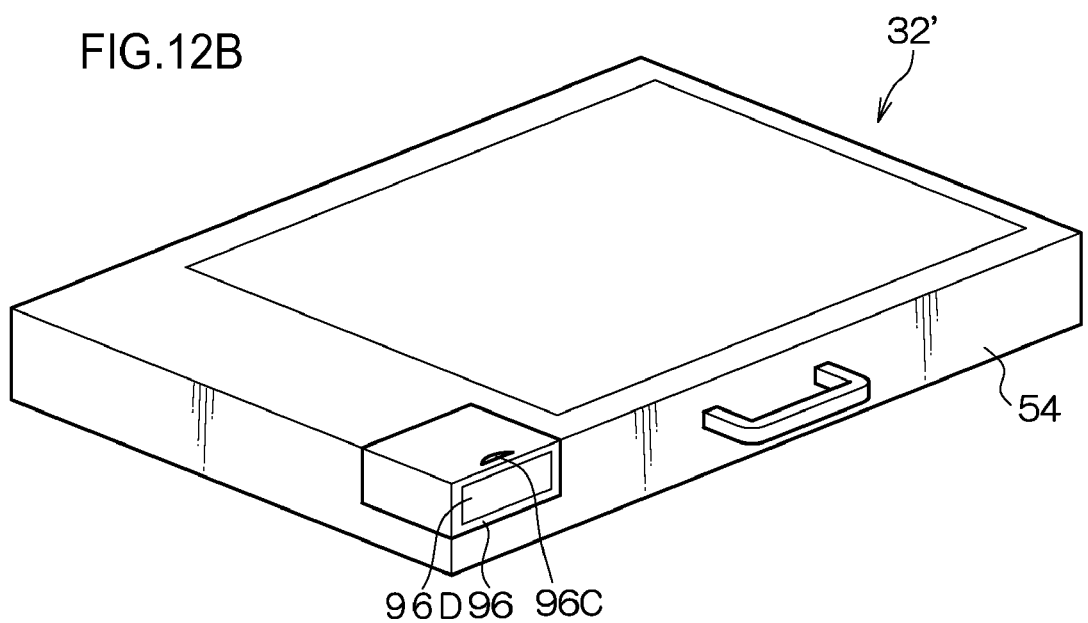

As shown in FIG. 12A and FIG. 12B, a space region 32D, which has the approximately the same shape as the outside shape of a corresponding power supplying apparatus 96, is formed at a corner of the electronic cassette 32' and the power supplying apparatus 96 is attached to the space region 32D.

In this case, the fixing member 32C and the urging member 32B, disposed in the electronic cassette 32 as shown in FIG. 5 to easily remove the power supplying apparatus 96, need not be provided. Therefore, such case can realize a weight reduction and a cost reduction of the electronic cassette.

In the above case, the display section 96D is not necessary to be provided in the side face where the recessed portion 96C of the power supplying apparatus 96, as shown in FIG. 5, is provided. For example, the display section 96D may be provided in another face that appears in the surface when it is mounted to the electronic cassette 32 (the state shown in FIG. 12B) such as the face in which the recessed portion 96C is provided (top face shown in FIG. 12A and FIG. 12B). The same advantage as that of the exemplary embodiment can be achieved in the above case.

Further, in the exemplary embodiment, a case has been explained where the image data obtained by radiation imaging is stored, is passed to the receptionist by the examinee. However, the present invention is not limited thereto. For example, in an alternative exemplary embodiment, the radiological technologist can directly pass the power supplying apparatus 96 to the receptionist. The same advantage as that of the exemplary embodiment can be achieved in the alternative exemplary embodiment.

Further, in the exemplary embodiment, a case has been explained where the radiation imaging is inhibited by the console 42. However, the present invention is not limited thereto. For example, in an alternative exemplary embodiment, the radiation imaging may be inhibited by the electronic cassette 32. In the alternative exemplary embodiment, a display section may be an audio combined device that can be disposed on the electronic cassette 32. In addition to the above configuration, in the alternative exemplary embodiment, the imaging order information (refer to FIG. 7) previously stored in the memory 92B or the storage section 92C, and instruction information for instructing an execution of radiation imaging, is transmitted to the console 42 by the cassette controller 92 of the electronic cassette 32 in place of step 308 to step 320 of the radiation imaging process program (refer to FIG. 10). In this case, in step 324, the display section displays (visually displays when the display section is the display and audibly displays when the display section is the audio combining device) the predetermined information (as an example, the information shown in FIG. 11B) showing that an examinee may be misidentified. On the other hand, when the instruction information for instructing the execution of the radiation imaging is received, the console 42 executes the same steps as step 308 to step 320. Accordingly, the same advantage as that of the above exemplary embodiment can be also achieved in the alternative exemplary embodiment.

Further, in the exemplary embodiment, a case has been explained where the present invention is applied to the electronic cassette. However, the present invention is not limited thereto. For example, an ordinary cassette for imaging a radiation image by a radiation film, an IP cassette for imaging a radiation image by an imaging plate, and the like, can be applied as apparatus for imaging a radiation image.

Further, in the exemplary embodiment, a case has been explained where the radiation imaging apparatus of the present invention is applied to the portable electronic cassette. However, the present invention is not limited thereto. For example, the present invention may be applied to a so-called built-in type radiation imaging apparatus fixedly disposed in the rack 45, the bed 46, and the like. The same advantage as that of the exemplary embodiment can be also achieved in this case.

Further, in the exemplary embodiment, a case has been explained where all the examinee information is stored to the memory 96B of the power supplying apparatus 96. However, the present invention is not limited thereto. For example, in an alternative exemplary embodiment, minimum information capable for specifying an examinee, such as his or her name, ID, and the like, may be stored. The same advantage as that of the exemplary embodiment may be also achieved in the alternative exemplary embodiment.

In the exemplary embodiment, a case has been explained where the radiological technologist sets various settings for radiation imaging by using the imaging order information held by the console 42. However, the present invention is not limited thereto. An alternative exemplary embodiment may be configured to set various settings for radiation imaging by using the examinee information displayed on the display section 96D of a usable power supplying apparatus mounted to the electronic cassette 32. In this alternative exemplary embodiment, displaying the imaging order information on the console 42 can be omitted. Accordingly, the above alternative exemplary embodiment can improve the convenience of the user.

In the exemplary embodiment, the case has been explained where information to be displayed has been transferred to the display section 96D of the power supplying apparatus 96 via the charging apparatus 40. However, in place of the charging apparatus 40, the information may be stored (transferred) into the memory 96B of the power supplying apparatus 96 in a non-contact manner by using RFID (Radio Frequency Identification) technique or the like. The same advantage as that of the above exemplary embodiment can be also achieved in this case.

Further, in the exemplary embodiment, a case has been explained where the secondary battery is applied as the power supply section of the present invention. However, the present invention is not limited thereto. Capacitors such as an electric field capacitor, an electric double-layer capacitor, a lithium-ion capacitor, and the like, may be applied as the power supply section of the present invention. The same advantage as that of the above exemplary embodiment can be also achieved in this case.

Further, in the exemplary embodiment, a case has been explained where the power supplying apparatus including the secondary battery is applied as the power supplying apparatus of the present invention. However, the present invention is not limited thereto. A fuel battery may be applied as the power supplying apparatus of the present invention. Note that, in this case, a filling section for filling fuel, such as alcohol water, ammonia water, and the like, will correspond to the power supply section of the present invention. The same advantage as that of the exemplary embodiment may also be achieved accordingly.

Further, in the exemplary embodiment, a case has been explained where the power supply section of the present invention is fixedly assembled as the power supplying apparatus of the present invention. However, the present invention is not limited thereto. In an alternative exemplary embodiment, the power supply section may be detachably mounted to the power supplying apparatus. The same advantage as that of the exemplary embodiment may also be achieved in the alternative exemplary embodiment.

Further, in the exemplary embodiment, a case has been explained where, when the examinee information received by the console 42 does not match with the imaging order information, the process to inhibit imaging of the imaging subject performed by the electronic cassette 32 is executed. However, the present invention is not limited thereto. Alternative exemplary embodiment may employ where a process for notifying occurrence of failure is executed and where both the process for notifying the occurrence of failure and the process for inhibiting the imaging are executed. Note that, as the process for notifying the occurrence of failure, a process of displaying the occurrence of failure by the display 100, a process of providing the electronic cassette 32 with a sounding section such as a buzzer and sounding the sounding section, may be exemplified. The same advantage as that of the above exemplary embodiment may be achieved also in the alternative exemplary embodiment.

Further, in the exemplary embodiment, a case has been explained where the charging apparatus 40 connected to the in-hospital network 16 via the commercial power source line. However, the present invention is not limited thereto. As, for example, in an alternative exemplary embodiment, the charging apparatus 40 may be connected to the in-hospital network 16 through wireless LAN. The use of the wireless LAN permits the charging apparatus 40 to be installed to any location where the charging apparatus 40 can communicate through the wireless LAN. As a result, the alternative exemplary embodiment can also prevent the misidentification.

In addition to the above mentioned, note that, the configuration of the RIS 10 (refer to FIG. 1), the configuration of the radiation imaging room 44 (refer to FIG. 2), the configuration of the electronic cassette 32 (refer to FIGS. 3 and 5), the configuration of the charging apparatus 40 (refer to FIG. 4), and the configuration of the imaging system 18 (refer to FIG. 6) explained in the exemplary embodiment, are examples. It is needless to say that deletes of unnecessary portions, addition of new portions, and change in the connection state, which does not depart from the gist of the present invention, is in the scope of the present invention.

Further, note that, the configuration of the imaging order information explained in the exemplary embodiment (refer to FIG. 7) is an example. It is needless to say that delete of unnecessary information, addition of new information, and change of the information, which does not depart from the gist of the present invention, is within the scope of the present invention.

Further, note that, the flows of the processes of the examinee information writing process program and the radiation imaging process program explained in the exemplary embodiment (refer to FIGS. 8 and 10) are examples. It is needless to say that, delete of unnecessary steps, addition of new steps, and replacement of processing sequences, which does not depart of the gist of the present invention, is within the scope of the present invention.

Further, note that, the display information explained in the exemplary embodiment (refer to FIGS. 9 and 11) is also an example. Further, it is needless to say that the contents of the display may be changed.

What is claimed is:

1. A radiation imaging system comprising:
   a radiation imaging apparatus that images a radiation image represented by radiation that passes through an imaging subject; and
   a power supplying apparatus, mounted detachably to the radiation imaging apparatus, and including a chargeable power supply section that supplies drive power to the radiation imaging apparatus, and a display section that displays an imaging subject information associated with the imaging subject.

2. The radiation imaging system according to claim 1, wherein the power supplying apparatus further includes a storing section that stores the imaging subject information, and
   wherein the display section displays the stored imaging subject information.

3. The radiation imaging system according to claim 2, further comprising a charging apparatus including,
   a charging section that charges the power supplying apparatus when the power supplying apparatus is mounted to the charging apparatus, and
   a writing section that writes the imaging subject information into the storing section when the power supplying apparatus is mounted to the charging apparatus, before the power supplying apparatus is mounted to the radiation imaging apparatus.

4. The radiation imaging system according to claim 3, wherein the storing section further stores image information obtained by imaging performed by the radiation imaging apparatus, and
   wherein the charging apparatus further includes a reading section that reads the stored image information when the power supplying apparatus is mounted.

5. The radiation imaging system according to claim 3, wherein the radiation imaging apparatus further comprises:
   a transmitting section that, before the imaging subject is imaged, transmits the stored imaging subject information when the power supplying apparatus is mounted to the radiation imaging apparatus;
   a receiving section that receives the transmitted imaging subject information;
   a determining section that determines whether the received imaging subject information is information that corresponds to the imaging subject; and
   a process executing section that executes a predetermined process based on the result of the determination.

6. The radiation imaging system according to claim 5, wherein, when it is determined that the imaging subject information is not the information that corresponds to the imaging subject, the process execution section executes at least one of an imaging inhibition process or an occurrence of failure notification process as the predetermined process.

7. The radiation imaging system according to claim 5, wherein the determination section determines whether the received imaging subject information is the information that corresponds to the imaging subject by determining whether the imaging subject information matches with the imaging subject information written in the storing section.

8. The radiation imaging system according to claim 3, wherein the imaging subject information includes specific information for specifying the imaging subject.

9. The radiation imaging system according to claim 8, wherein the imaging subject information further includes information showing an imaging condition of the imaging subject.

10. The radiation imaging system according to claim 3, wherein the charging apparatus further includes a detachment inhibiting section that inhibits detachment of the power supplying apparatus when charging of the power supply section has not been completed when the power supplying apparatus is mounted to the charging apparatus.

11. The radiation imaging system according to claim 3, wherein the charging apparatus further includes a communication section that performs communication through a power line of a commercial power source.

12. The radiation imaging system according to claim 1, wherein the radiation imaging apparatus is an electronic cassette.

13. A power supplying apparatus comprising:
a chargeable power supply section that supplies drive power to a radiation imaging apparatus that images a radiation image represented by radiation that passes through an imaging subject; and
a display section that displays imaging subject information associated with the imaging subject,
wherein the power supplying apparatus is mounted detachably to the radiation imaging apparatus.

14. A charging apparatus comprising:
a charging section that charges a chargeable power supply section of a power supplying apparatus when the power supplying apparatus is mounted to the charging apparatus, the power supplying apparatus including,
the power supply section that supplies drive power to the radiation imaging apparatus that images a radiation image represented by radiation that passes through an imaging subject,
a display section that displays imaging subject information associated with the imaging subject,
a storing section that stores the imaging subject information; and
a writing section that writes the imaging subject information into the storing section when the power supplying apparatus is mounted to the charging apparatus, before the power supplying apparatus is mounted to the radiation imaging apparatus.

15. A method for radiation imaging in a radiation imaging system including a radiation imaging apparatus that images a radiation image represented by radiation that passes through an imaging subject, a power supplying apparatus, mounted detachably to the radiation imaging apparatus, and including a chargeable power supply section that supplies drive power to the radiation imaging apparatus, a display section that displays imaging subject information associated with the imaging subject, and a storing section that stores the imaging subject information, a charging apparatus including a charging section that charges the power supplying section when the power supplying apparatus is mounted to the charging apparatus, the method comprising:
writing the imaging subject information in the storing section by the charging apparatus when the power supplying apparatus is mounted to the charging apparatus, before the power supplying apparatus is mounted to the radiation imaging apparatus;
transmitting the imaging subject information to the radiation imaging apparatus when the power supplying apparatus is mounted to the radiation imaging apparatus, before an imaging subject is imaged;
receiving the transmitted the imaging subject information;
determining whether the received imaging subject information corresponds to the imaging subject; and
executing a predetermined process based on a result of the determination.

* * * * *